United States Patent
Barnidge et al.

(10) Patent No.: US 11,209,439 B2
(45) Date of Patent: Dec. 28, 2021

(54) IDENTIFICATION OF IMMUNOGLOBULIN FREE LIGHT CHAINS BY MASS SPECTROMETRY

(71) Applicant: Mayo Foundation for Medical Education and Research, Rochester, MN (US)

(72) Inventors: David R. Barnidge, Rochester, MN (US); David L. Murray, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 176 days.

(21) Appl. No.: 15/762,900

(22) PCT Filed: Sep. 26, 2016

(86) PCT No.: PCT/US2016/053675
§ 371 (c)(1),
(2) Date: Mar. 23, 2018

(87) PCT Pub. No.: WO2017/053932
PCT Pub. Date: Mar. 30, 2017

(65) Prior Publication Data
US 2018/0267057 A1    Sep. 20, 2018

Related U.S. Application Data

(60) Provisional application No. 62/232,182, filed on Sep. 24, 2015.

(51) Int. Cl.
*G01N 33/68* (2006.01)
*C07K 16/00* (2006.01)

(52) U.S. Cl.
CPC ......... *G01N 33/6857* (2013.01); *C07K 16/00* (2013.01); *G01N 33/6848* (2013.01);
(Continued)

(58) Field of Classification Search
None
See application file for complete search history.

(56) References Cited

U.S. PATENT DOCUMENTS 8,501,907 B2   8/2013   Jordan et al.
8,679,767 B2   3/2014   Kaur et al.
(Continued)

FOREIGN PATENT DOCUMENTS

EP   1329719   7/2003
EP   3270154   1/2018
(Continued)

OTHER PUBLICATIONS

Barnidge, D.R., et al. Using Mass Spectrometry to Monitor Monoclonal Immunoglobulins in Patients with a Monoclonal Gammopathy, Journal of Proteome Research, 13, 1419-1427 (Year: 2014).*

(Continued)

*Primary Examiner* — Xiaoyun R Xu
(74) *Attorney, Agent, or Firm* — Fish & Richardson P.C.

(57) ABSTRACT

This document relates to methods for identifying one or more immunoglobulin free light chains in a sample using mass spectrometry. For example, this document relates to a method for identifying one or more immunoglobulin free light chains in a sample that includes (a) providing a sample; (b) subjecting the sample to a mass spectrometry technique to obtain a mass spectrum of the sample; and (c) identifying the presence of the one or more immunoglobulin free light chains.

22 Claims, 18 Drawing Sheets

(52) U.S. Cl.
CPC .... *C07K 2317/515* (2013.01); *G01N 2800/22* (2013.01); *G01N 2800/50* (2013.01); *G01N 2800/52* (2013.01); *G01N 2800/7047* (2013.01)

(56) References Cited

U.S. PATENT DOCUMENTS

| | | |
|---|---|---|
| 2002/0182649 A1 | 12/2002 | Weinberger et al. |
| 2003/0027216 A1 | 2/2003 | Kiernan et al. |
| 2005/0009009 A1 | 1/2005 | Peiris et al. |
| 2005/0064422 A1 | 3/2005 | Barnidge et al. |
| 2006/0024296 A1 | 2/2006 | Williams |
| 2006/0281122 A1 | 12/2006 | Bryant |
| 2007/0015222 A1 | 1/2007 | Kaneko et al. |
| 2007/0054407 A1 | 3/2007 | Chen et al. |
| 2007/0105181 A1 | 5/2007 | Pope et al. |
| 2007/0184470 A1 | 8/2007 | Arman et al. |
| 2007/0259398 A1 | 11/2007 | Arnott et al. |
| 2007/0292441 A1 | 12/2007 | Glover et al. |
| 2008/0026949 A1 | 1/2008 | Hoidal et al. |
| 2008/0064055 A1 | 3/2008 | Bryant |
| 2008/0142696 A1 | 6/2008 | Geromanos et al. |
| 2008/0171312 A1 | 7/2008 | Ley et al. |
| 2008/0317745 A1 | 12/2008 | Boruchov et al. |
| 2009/0186423 A1 | 7/2009 | Frandsen |
| 2009/0203602 A1 | 8/2009 | Gelber et al. |
| 2009/0258828 A1 | 10/2009 | Beuerman et al. |
| 2010/0015652 A1 | 1/2010 | Granda et al. |
| 2010/0086922 A1 | 4/2010 | Bryant |
| 2010/0167267 A1 | 7/2010 | Schulzknappe et al. |
| 2010/0190652 A1 | 7/2010 | Nagalla et al. |
| 2010/0323381 A1 | 12/2010 | Bergen, III et al. |
| 2011/0065199 A1 | 3/2011 | Kuge et al. |
| 2011/0117021 A1 | 5/2011 | Smith et al. |
| 2011/0151494 A1 | 6/2011 | Koomen et al. |
| 2011/0183426 A1 | 6/2011 | Chan et al. |
| 2011/0294150 A1 | 12/2011 | Koll et al. |
| 2012/0309040 A1 | 12/2012 | Madian et al. |
| 2012/0315645 A1 | 12/2012 | Kaur et al. |
| 2012/0322073 A1 | 12/2012 | Lopez-Girona |
| 2013/0040851 A1 | 2/2013 | Hanzawa et al. |
| 2013/0149389 A1 | 6/2013 | Flora et al. |
| 2013/0178370 A1 | 7/2013 | Lavinder et al. |
| 2013/0178385 A1 | 7/2013 | Bahn et al. |
| 2013/0185096 A1 | 7/2013 | Giusti |
| 2013/0260406 A1 | 10/2013 | Koomen et al. |
| 2014/0045276 A1 | 2/2014 | Singh et al. |
| 2014/0186332 A1 | 7/2014 | Ezrn et al. |
| 2014/0242072 A1 | 8/2014 | Hansson |
| 2014/0242624 A1 | 8/2014 | Valliere-Douglass |
| 2014/0249049 A1 | 9/2014 | Stoll et al. |
| 2015/0204884 A1 | 7/2015 | Robblee |
| 2015/0219665 A1 | 8/2015 | Chapple et al. |
| 2015/0276771 A1 | 10/2015 | Madasamy |
| 2015/0340219 A1 | 11/2015 | Mellors |
| 2015/0362506 A1 | 12/2015 | Zhu et al. |
| 2016/0033511 A1 | 2/2016 | Pannell et al. |
| 2016/0041184 A1 | 2/2016 | Barnidge et al. |
| 2016/0047819 A1 | 2/2016 | Viscom et al. |
| 2016/0206660 A1 | 7/2016 | Shi et al. |
| 2016/0231329 A1 | 8/2016 | Olsson et al. |
| 2016/0257763 A1 | 9/2016 | Von Kreudenstein et al. |
| 2016/0349269 A1 | 12/2016 | Hunt et al. |
| 2017/0023584 A1 | 1/2017 | Murray et al. |
| 2017/0044608 A1 | 2/2017 | Wang et al. |
| 2017/0205423 A1 | 7/2017 | Higel et al. |
| 2017/0336419 A1 | 11/2017 | Tran et al. |
| 2018/0106815 A1 | 4/2018 | Barnidge et al. |
| 2019/0195888 A1 | 6/2019 | Barnidge et al. |
| 2020/0003784 A1 | 1/2020 | Murray et al. |

FOREIGN PATENT DOCUMENTS

| | | |
|---|---|---|
| SG | 183701 | 9/2012 |
| WO | WO 2005/101017 | 10/2005 |
| WO | WO 2008/057083 | 12/2006 |
| WO | WO 2006138629 | 12/2006 |
| WO | WO 2010/119295 | 10/2010 |
| WO | WO 2011/077129 | 6/2011 |
| WO | WO 2012/056232 | 5/2012 |
| WO | WO 2013/049410 | 4/2013 |
| WO | WO 2013096451 | 6/2013 |
| WO | WO 2013/185180 | 12/2013 |
| WO | WO 2014/078374 | 5/2014 |
| WO | WO 2014/105985 | 7/2014 |
| WO | WO 2014109927 | 7/2014 |
| WO | WO 2014/121031 | 8/2014 |
| WO | WO 2014150170 | 9/2014 |
| WO | WO 2015/131169 | 9/2015 |
| WO | WO 2015154052 | 10/2015 |
| WO | WO 2016018978 | 2/2016 |
| WO | WO 2016/134365 | 8/2016 |
| WO | WO 2016/172485 | 10/2016 |
| WO | WO 2017022315 | 2/2017 |
| WO | WO 2017/134274 | 8/2017 |
| WO | WO 2017/144903 | 8/2017 |
| WO | WO 2017/180735 | 10/2017 |
| WO | WO 2017/205694 | 11/2017 |
| WO | WO 2018/049001 | 3/2018 |

OTHER PUBLICATIONS

Extended European Search Report in European Application No. 16849839.2 dated May 23, 2019, 10 pages.

Abcam, "Understanding secondary antibodies" 2012, 12 pages, downloaded from http://docs.abcam.com/pdf/general/understanding_secondary_antibodies.pdf.

"Abraham et al.,""Characterization of free immunoglobulin light chains (LC) by mass spectrometry in light chain-associated (AL) amyloidosis,""American Society of Hematology 43rd Annual Meeting, part 2, Orlando, Florida, USA, 98(11 Pt 2), p. 31b, Abstract#3722, Nov. 16, 2001".

Abraham et al., "Trimolecular complexes of lambda light chain dimers in serum of a patient with multiple myeloma," Clin Chem., 48(10):1805-1811, Oct. 2002.

Adamczyk et al., "Profiling of polyclonal antibody light chains by liquid chromatography/electrospray ionization mass spectrometry," Rapid Commun Mass Spectrom., 14:49-51, 2000.

Adamczyk et al.,"Papain digestion of different mouse IgG subclasses as studied by electrospray mass spectrometry," J Immun Methods., 237:95-104, 2000.

Anonymous: "KappaSelect LambdaFabSelect," Data File 28-9448-22 AB, Mar. 1, 2012, Retrieved from the Internet: URL: https://www.gelifesciences.co.jp/catalog/pdf/Kappaselect_LamdaFabSelect.pdf Retrieved on Sep. 22, 2017, 4 pages.

Arun et al., "Immunohistochemical examination of light-chain expression (lambda/kappa ratio) in canine, feline, equine, bovine and porcine plasma cells," Zentralbl Veterinarmed A., 43(9):573-576, Nov. 1996.

"Aucouturier et al.,""Monoclonal immunoglobulin light chains associated to Fanconi's syndrome,""Monoclonal Gammopathies and the Kidney, 2003, 87-92".

Barnidge et al., "Monitoring M-proteins in patients with multiple myeloma using heavy-chain variable region clonotypic peptides and LC-MS/MS," J Proteome Res., 13(4):1905-1910, Epub Mar. 5, 2014.

Barnidge et al., "Phenotyping polyclonal kappa and lambda light chain molecular mass distributions in patient serum using mass spectrometry," J Proteome Res., 13(11):5198-5205, Epub Aug. 26, 2014.

Barnidge et al., "Using MALDI-TOF MS to Screen for Monoclonal Gammopathies in Serum and Urine," 61st Annual ASMS Conference on Mass Spectrometry and Allied Topics, Minneapolis, MN, Jun. 9-13, 2013, 1 page poster.

Barnidge et al., "Using mass spectrometry to monitor monoclonal immunoglobulins in patients with a monoclonal gammopathy," J Proteome Res., 13(3): 1419-1427, Epub Feb. 11, 2014.

(56) References Cited

OTHER PUBLICATIONS

Barnidge, "Monitoring specific IgG tryptic peptides in multiple myeloma using the TripleTOFtm 5600 System," AB SCIEX Annual Users Meeting at ASMS, May 20, 2012, 28 slides.
Bennett et al., "Monitoring papain digestion of a monoclonal antibody by electrospray ionization mass spectrometry," Analytical Biochemistry., 245:17-27,1997.
Berg et al., "Mass spectrometry based proteomic analysis identifies two distinct types of cutaneous amyloidosis," Mod Pathol., vol. 22; p. 100A, 2009.
Bergen et al., "Characterization of amyloidogenic immunoglobulin light chains directly from serum by on-line immunoaffinity isolation," Biomedical Chromatography, 18(3): 191-201, Apr. 1, 2004.
Bergon et al., "Linearity and detection limit in the measurement of serum M-protein with the capillary zone electrophoresis system Capillarys," Clinical Chemistry and Laboratory Medicine, 43:721-723, 2005.
Bermudez-Crespo et al., "A better understanding of molecular mechanisms underlying human disease," Proteomics Clinical Applications, 1:983-1003, 2007.
Biosis accession No. PREV200200151435, 2 pages, Nov. 2001 Abstract only.
Biosis accession No. PREV201100424453, 2 pages, Nov. 2010 Abstract only.
Bois et al., "Cutaneous amyloidosis: mass spectrometry based proteomic analysis reveals diverse etiology associated with unique histopathological features," Mod Pathol., 26:320A-321A, Feb. 2013.
Boissinot et al., "Up-Regulation of Anti-Inflammatory, STAT3-Activating Hepatocyte Growth Factor and Interleukin-11 In Polycythemia Vera Is Independent of JAK2V617F and Contributes to the Growth of Clonal Erythroblasts," Blood, 116(21):796, Nov. 2010, 52nd Annual Meeting of the American Society of Hematology, Orlando, FL, USA Dec. 4-7, 2010.
Bondarenko et al., "Mass measurement and top-down HPLC/MS analysis of intact monoclonal antibodies on a hybrid linear quadrupole ion trap-orbitrap mass spectrometer," J Am Soc Mass Spectrometry., 20:1415-1424, 2009.
Bourell et al., "Electrospray ionization mass spectrometry of recombinantly engineered antibody fragments," Anal Chem., 66:2088-2095, 1994.
Bradwell et al., "Highly sensitive, automated immunoassay for immunoglobulin free light chains in serum and urine," Clin Chem., 47(4):673-680, Apr. 2001.
Brochet et al., "IMGT/V-QUEST: the highly customized and integrated system for IG and TR standardized V-J and V-D-J sequence analysis," Nucleic Acids Res., 36(Web Server issue):W503-W508, Epub May 24, 2008.
Butler et al., "Immunoglobulins, antibody repertoire and B cell development," Dev Comp Immunol., 33(3):321-333, Epub Sep. 18, 2008.
Chen et al., "Characterization of protein therapeutics by mass spectrometry: recent developments and future directions," Drug Discovery Today., 16:58-64, 2011.
Cheung et al., "A proteomics approach for the identification and cloning of monoclonal antibodies from serum," Nature Biotechnology., 30:447-452, 2012.
Cohen., "Antibody structure," J Clin Path., 28 Suppl, 6:1-7, 1975.
Cordoba et al., "Non-enzymatic hinge region fragmentation of antibodies in solution," J Chromatography B., 818:115-121, 2005.
De Costa et al., "Sequencing and Quantifying IgG Fragments and Antigen-Binding Regions by Mass Spectrometry" Journal of Proteome Research, 9:2937-2945, Epub Apr. 14, 2010.
Dekker et al., "An Antibody-Based Biomamarker Discovery Method by Mass Spectrometry Sequencing of Complementarity Determining Regions," Analytical and Bioanalytical Chemistry, 399:1081-1091, 2011.
Dogan et al., "Leukocyte Chemotactic Factor 2 Amyloidosis: A Novel Type of Amyloidosis That Mimics AL Amyloidosis," presented at The United States and Canadian Academy of Pathology Annual Meeting, Mar. 2009, 1 page.

Extended European Search Report in Application No. 18174068.9, dated Jul. 10, 2018, 9 pages.
Extended European Search Report in European Application No. 15827198.1, dated Nov. 23, 2017, 12 pages.
Favereaux et al., "Serum IgG antibodies to P0 dimer and 35 kDa P0 related protein in neuropathy associated with monoclonal gammopathy," J Neurol Neurosurg Psychiatry., 74:1262-1266, 2003.
Fortini et al., "Cerebrospinal fluid oligoclonal bands in the diagnosis of multiple sclerosis. Isoelectric focusing with IgG immunoblotting compared with high-resolution agarose gel electrophoresis and cerebrospinal fluid IgG index," Am J Clin Pathol., 120(5):672-675, Nov. 2003.
Frangione, B., "Structure of Human lmmuniglobulins and their Variants" B. Benacerraf (ed) lmmunogenetics and Immunodeficiency, 1-53, 1975.
Gebski et al., "Affinity chromatography applications with single-domain antibodies," Bioprocess International., Aug. 1, 2013, Retrieved from the Internet: URL: http://www.bioprocessintl.com/2013/affinity-chromatography-applications-with-single-domain-antibodies-345480/ Retrieved on Sep. 22, 2017.
GenBank Accession AAA59107, "immunoglobulin lambda light chain C2 region, partial [*Homo sapiens*]," May 4, 2000, 2 pages.
Hagman et al., "Absolute quantification of monoclonal antibodies in biofluids by liquid chromatography-tandem mass spectrometry," Analytical Chemistry, 80(4):1290-1296, Feb. 15, 2008.
Hagmann et al., "Characterization of the F(ab')2 fragment of a murine monoclonal antibody using capillary isoelectric focusing and electrospray ionization mass spectrometry," J Chromatography A., 816:49-58, 1998.
Haraldsson et al., "Determination of kappa and lambda light chains in serum immunoglobulins G, A and M," Ann Clin Biochem., 28 ( Pt 5):461-466, Sep. 1991.
Heudi et al., "Towards absolute quantification of therapeutic monoclonal antibody in serum by LC-MS/MS using isotope-labeled antibody standard and protein cleavage isotope dilution mass spectrometry," Anal Chem., 80(11):4200-4207, Epub May 9, 2008.
Hieter et al., "Clustered arrangement of immunoglobuling constant region genes in man," Nature, 294:536-540, 1981.
Hsieh et al., "Elucidation of potential bortezomib response markers in multiple myeloma patients," Journal of Pharmaceutical and Biomedical Analysis, 49:115-122, 2009.
International Preliminary Report on Patentability for PCT/US2015/024379, dated Oct. 13, 2016, 10 pages.
International Preliminary Report on Patentability for PCT/US2015/042580, dated Jan. 31, 2017, 10 pages.
International Search Report and Written Opinion for PCT/US2016/53675, dated Feb. 28, 2017, 15 pages.
Jagannath et al., "Value of serum free light chain testing for the diagnosis and monitoring of monoclonal gammopathies in hematology," Clin Lymphoma Myeloma, 7(8):518-523, Sep. 2007.
Jemal et al., "Cancer statistics, 2003," CA Cancer J Clin., 53(1):5-26, Jan.-Feb. 2003.
Jones et al., "A protocol for 'enhanced pepsin digestion': a step by step method for obtaining pure antibody fragments in high yield from serum," J of Immunol Methods., 275:239-250, 2003.
Joosten et al., "The production of antibody fragments and antibody fusion proteins by yeasts and filamentous fungi," Microbial Cell Factories., 2:1, 15 pages, 2003.
Kabat et al., "An electrophoretic study of the protein components in cerebrospinal fluid and their relationship to the serum proteins," J Clin Invest., 21(5):571-577, Sep. 1942.
Kaltashov et al., "Advances and challenges in analytical characterization of biotechnology products: Mass spectrometry-based approaches to study properties and behavior of protein therapeutics," Biotechnology Advances., 30:210-222, 2012.
Kaplan et al., "Free light chains in plasma of patients with light chain amyloidosis and non-amyloid light chain deposition disease. High proportion and heterogeneity of disulfide-linked monoclonal free light chains as pathogenic features of amyloid disease," British Journal of Haematology., 144(5):705-715, 2008.
Katzmann et al., "Serum reference intervals and diagnostic ranges for free kappa and free lambda immunoglobulin light chains:

(56) References Cited

OTHER PUBLICATIONS relative sensitivity for detection of monoclonal light chains," Clin. Chem., 48(9): 1437-44, Sep. 2002.
Kohlhagen, "Using MALDI-TOF MS to Screen for Monoclonal Proteins in Serum," The Association for Mass Spectrometry Applications to the Clinical Lab [online] 2015. Retrieved from the Internet: <URL: https://www.msacl.org/2015_US_Long_Abstracts/201412041312_53747.pdf>, MSACL 2015 US: Preliminary Conference Program, San Diego, CA, Mar. 28-Apr. 1, 2015, 2 pages.
Koomen et al., "Proteomic contributions to personalized cancer care," Molecular & Cellular Proteomics, 7.10:1780-1794, 2008.
Kowarik et al., "The cerebrospinal fluid immunoglobulin transcriptome and proteome in neuromyelitis optica reveals central nervous system-specific B cell populations," J Neuroinflammation., 12:19, Jan. 28, 2015.
Kroon et al., "Identification of sites of degradation in a therapeutic monoclonal antibody by peptide mapping," Pharmaceutical Research., 9:1386-1393, 1992.
Ladwig et al., "Quantification of serum IgG subclasses by use of subclass-specific tryptic peptides and liquid chromatography-tandem mass spectrometry," Clin Chem., 60(8): 1080-1088, May 5, 2014.
Landgren et al., "Monoclonal gammopathy of undetermined significance (MGUS) consistently precedes multiple myeloma: a prospective study" Blood, 113(22):5412-5417, May 28, 2009.
Lavatelli et al., "A novel approach for the purification and proteomic analysis of pathogenic immunoglobulin free light chains from serum," Biochimica rt Biophysica Acta., 1814(3):409-419, Dec. 28, 2010.
Lebeau et al., "Generalized crystal-storing histiocytosis associated with monoclonal gammopathy: molecular analysis of a disorder with rapid clinical course and review of the literature," Blood., 100:1817-1827, 2002.
Lefranc, "IMGT, the International ImMunoGeneTics Information System," Cold Spring Harb Protoc., 2011(6):595-603, Jun, 1, 2011.
Leung et al., "Monoclonal gammopathy of renal significance: when MGUS is no longer undetermined or insignificant," Blood, 120:4292-4295, 2012.
Li et al., "General LC-MS/MS method approach to quantify therapeutic monoclonal antibodies using a common whole antibody internal standard with application to preclinical studies," Analytical Chemistry, 84:1267-1273, 2012.
Li et al., "Simultaneous analysis of multiple monoclonal antibody biotherapeutics by LC-MS/MS method in rat plasma following cassette-dosing," AAPS J., 15(2):337-346, Epub Dec. 12, 2012.
Lindop et al., "Molecular signature of a public clonotypic autoantibody in primary Sjogren's syndrome: A "forbidden" clone in systemic autoimmunity," Arthritis & Rheumatism., 63(11):3477-3486, Oct. 28, 2011.
Liu et al., "Quantitation of a recombinant monoclonal antibody in monkey serum by liquid chromatography-mass spectrometry," Anal Biochem., 414(1): 147-153, Epub Mar. 8, 2011.
Lu et al., "Detection of abundant proteins in multiple myeloma cells by proteomics," J Proteomics Bioinform., 3(1):005-009, 2010.
Lu et al., "LC-MS Analysis of Polyclonal Human Anti-Neu5Gc Xeno-Autoantibodies Immunoglobulin G Subclass and Partial Sequence Using Multistep Intravenous Immunoglobulin Affinity Purification and Multienzymatic Digestion," Analytical Chemistry., 84(6):2761-2768, Mar. 20, 2012.
McBride et al., "Chromosomal location of human kappa and lambda immunoglobulin light chain constant region genes," J Exp Med., 155(5): 1480-1490, May 1, 1982.
Merlini and Palladini, "Differential diagnosis of monoclonal gammopathy of undetermined significance" Hematology, 595-603, 2012.
Mukhopadhyay et al., "A tribute to Frank Anscombe and random central limit theorem from 1952," Sequential Analysis, 31(3): 265-277, 2012.
Murphy et al., "Characterization of systemic amyloid deposits by mass spectrometry," Methods Enzymol., 412:48-62, 2006.

Nasr et al., "Immunotactoid glomerulopathy: clinicopathologic and proteomic study," Nephrol Dial Transplant., 27(11):4137-4146, Epub Aug. 7, 2012.
Obermeier et al., "Matching of oligoclonal immunoglobulin transcriptomes and proteomes of cerebrospinal fluid in multiple sclerosis," Nat Med., 14(6):688-693, Epub May 18, 2008.
Pang et al., "Biomarker discovery in urine by proteomics," Journal of Proteome Research, 1:161-169, Epub Feb. 16, 2002.
Radovic, V. V.,"Recommendations For Use of Free Light Chain Assay in Monoclonal Gammopathies" Journal of Medical Biochemistry, 29:1-8, 2010.
Rajkumar et al., "Advances in the diagnosis, classification, risk stratification, and management of monoclonal gammopathy of undetermined significance: implications for recategorizing disease entities in the presence of evolving scientific evidence," Mayo Clinic Proceedings., 85:945-948, 2010.
Remily-Wood et al., "A database of reaction monitoring mass spectrometry assays for elucidating therapeutic response in cancer," Proteomics Clinical Applications, 5:383-396, 2011.
Ren et al., "Reversed-phase liquid chromatography-mass spectrometry of site-specific chemical modifications in intact immunoglobulin molecules and their fragments," J Chromatography A., 1179:198-204, 2008.
Rodriguez et al., "Immunoglobulin derived depositions in the nervous system: novel mass spectrometry application for protein characterization in formalin-fixed tissues," Lab Invest., 88(10):1024-1037, Epub Aug. 18, 2008.
Schaefer et al., "Residual serum monoclonal protein predicts progression-free survival in patients with previously untreated multiple myeloma," Cancer., 116:640-646, 2010.
Sethi et al., "Mass spectrometry-based proteomic diagnosis of renal immunoglobulin heavy chain amyloidosis," Clin J Am Soc Nephrol., 5:2180-2187, 2010.
Singh et al., "Cerebrospinal-fluid-derived immunoglobulin G of different multiple sclerosis patients shares mutated sequences in complementarity determining regions," Mol Cell Proteomics, 12(12):3924-3934, Epub Aug. 22, 2013.
Song et al., "Characterization of N-terminal processing of group VIA phospholipase A2 and of potential cleavage sites of amyloid precursor protein constructs by automated identification of signature peptides in LC/MS/MS analyses of proteolytic digests," J Am Soc Mass Spectrom., 15(12):1780-1793, Dec. 2004.
Stubbs et al., "Anti-neurofilament antibodies in neuropathy with monoclonal gammopathy of undetermined significance produce experimental motor nerve conduction block," Acta Neuropathology., 105:109-116, 2003.
Sun et al., "Immunoglobulin genes and diversity: what we have learned from domestic animals," J Anim Sci Biotechnol., 3(1): 18, Jun. 20, 2012.
Theis et al., "Immunoglobulin Light Chain Gene Constant Region Is An Invariable Part of Amyloid Deposits in AL Amyloidosis," Blood, 112(11):3128, Nov. 16, 2008.
Theis et al., "Mass spectrometry based proteomic analysis of AL amyloidosis: Immunoglobulin Light Chain Gene Constant Region Is An Invariable Part of Amyloid Deposits and provides valuable diagnostic target," presented at The United States and Canadian Academy of Pathology Annual Meeting, Mar. 2009, 1 page.
Thermo Scientific, "MelonTM Gel IgG Spin Purification Kit" [online], 2011 [retrieved on Aug. 6, 2015], Retrieved from the Internet: <URL: https://tools.lifetechnologies.com/content/sfs/manuals/MAN0011513_Melon_Gel_lgG_Spin_Purifi_UG.pdf>, 4 pages.
Thurgood et al., "An Immunodominant La/SSB autoantibody proteome derives from public clonotypes," Clinical and Experimental Immunology., 174:237-244, Oct. 6, 2013.
VanDuijn et al., "Immune responses are characterized by specific shared immunoglobulin peptides that can be detected by proteomic techniques," Journal of Biological Chemistry, 285:29247-29253, Jul. 8, 2010.
Verheesen et al., "Beneficial properties of single-domain antibody fragments for application in immunoaffinity purification and immunoperfusion chromatography," Biochim Biophys Acta., 1624(1-3):21-28, Dec. 5, 2003.

(56) References Cited

OTHER PUBLICATIONS

Vrana et al., "Amyloidosis typing based on Laser Microdissection and Mass Spectrometry of Paraffin-Embedded Tissue Biopsies" Companion to Peripheral Neuropathy, pp. 347-349, 2010.

Vrana et al., "Classification of Amyloidosis in Fat Aspiration Specimens Using Mass Spectrometry Based Proteomics," presented at The United States and Canadian Academy of Pathology Annual Meeting, Mar. 2009, 1 page.

Vrana et al., "Diagnosis and Classification of Amyloidosis in Abdominal Subcutaneous Fat Aspiration Specimens Using Mass Spectrometry Based Proteomics," Blood, 112(11):2710, Nov. 16, 2008.

Vrana et al., "Diagnosis and Typing of Cardiac Amyloidosis in Routine Clinical Specimens by Mass Spectrometry Based Proteomic Analysis," presented at The United States and Canadian Academy of Pathology Annual Meeting, Mar. 2009, 1 page.

Wang et al., "Construction of A Multiple Myeloma Diagnostic Model by Magnetic Bead-Based MALDI-TOF Mass Spectrometry of Serum and Pattern Recognition Software" Anatomical Record, 292:604-610, 2009.

Whiteaker et al., "Sequential multiplexed analyte quantification using peptide immunoaffinity enrichment coupled to mass spectrometry," Mol Cell Proteomics., 11(6):10.1074/mcp.M111.015347, 2012,10 pages.

Willrich et al., "Quantitation of infliximab using clonotypic peptides and selective reaction monitoring by LC-MS/MS," International Immunopharmacology., 28(1): 513-520, Sep. 1, 2015.

Willrich et al., "Serum infliximab quantitation by LC-MS/MS in patients treated for inflammatory disorders," Gastroenterology AGA Abstracts., Sal252, May 1, 2014, Retrieved from the internet: URL:https://ac.els-cdn.com/S0016508514608568/1-S2.0-S0016508514608568-main.pdf?_ti d=e58e3b4c-caOa-lle7-96b2-OOOO0aabOf6b&acdnat=1510753563_74ab7a6bOb5f976b8c948a995d894fce, Retrieved on Nov. 15, 2017, Abstract Only.

Zhang et al., "Characterization of variable regions of monoclonal antibodies by top-down mass spectrometry," Anal Chem., 79(15):5723-5729, 2007.

Abraham et al., "Correlation of serum immunoglobulin free light chain quantification with urinary Bence Jones protein in light chain myeloma," Clin. Chem., 48(4):655-657, Apr. 2002.

Alge et al., "Proteomic Analysis of Plasma Exosome-Associated Proteins Reveals That Differences In Kappa: Lambda Ratios Predict Severe Acute Graft-Versus-Host Disease Early After Allogeneic Hematopoietic Stem Cell Transplantation," Blood., 1278, Nov. 2010.

Alldridge et al., "Proteome profiling of breast tumors by gel electrophoresis and nanoscale electrospray ionization mass spectrometry," J. Proteome. Res., 7(4):1458-1469, Apr. 2008.

Aucouturier et al., "Monoclonal Ig L chain and L chain V domain fragment crystallization in myeloma-associated Fanconi's syndrome" J. Immunol., 150(8 Pt 1):3561-3568, Apr. 1993.

Barnidge and Murray, "Using Mass Spectrometry to Identify IgG Fc and Fab Fragments Produced by Plasmin in Patient Serum," Poster, Presented at American Society for Mass Spectrometry meeting on Jun. 7, 2016.

Barratt et al., "Urine proteomics: the present and future of measuring urinary protein components in disease," CMAJ, 177(4):361-368, Aug. 2007.

Bastian et al., "intra- and interchain disulfide bridges of the human J chain in secretory immunoglobulin A," Biol. Chem. Hoppe Seyler., 373(12): 1255-63, Dec. 1992.

Beck et al., "Characterization of therapeutic antibodies and related products," Anal. Chem., 85(2):715-736, Jan. 2013.

Breitkopf et al., "Detection of a rare BCR-ABL tyrosine kinase fusion protein in H929 multiple myeloma cells using immunoprecipitation (IP)-tandem mass spectrometry (MS/MS)," Proc. Natl. Acad. Sci. USA., 109(40): 16190-16195, Oct. 2012.

Chevreux et al., "Fast analysis of recombinant monoclonal antibodies using IdeS proteolytic digestion and electrospray mass spectrometry," Analytical Biochemistry, 415(2):212-214, Aug. 2011.

Chiasserini et al., "CSF proteome analysis in multiple sclerosis patients by two-dimensional electrophoresis," Eur. J. Neurol., 15(9):998-1001, Sep. 2008.

Chung et al., "Thermodynamic stability of a kappaI immunoglobulin light chain: relevance to multiple myeloma," Biophys. J., 88(6):4232-4242, Jun. 2005.

Coriu et al., "A molecular basis for nonsecretory myeloma," Blood, 104(3):829-831, Aug. 2004.

D'Aguanno et al., "Differential cerebro spinal fluid proteome investigation of Leber hereditary optic neuropathy (LHON) and multiple sclerosis," 193(1-2): 156-160, Dec. 2007.

Dannoc et al., "High resolution proteome analysis of cryoglobulins using Fourier transform-ion cyclotron resonance mass spectrometry," Proteomics, 3(8): 1425-1433, Aug. 2003.

De Lorenzi et al., "Urokinase links plasminogen activation and cell adhesion by cleavage of the RGD motif in vitronectin," EMBO reports, 17(7):982-98, Jul. 2016.

Dear et al., "Acquired dysfibrinogenemia caused by monoclonal production of immunoglobulin lambda light chain," Haematologica., 92(11):e 111-7, Nov. 2007.

Dillon et al., "Optimization of a reversed-phase high-performance liquid chromatography/mass spectrometry method for characterizing recombinant antibody heterogeneity and stability," J. Chromatogr. A., 1120(1-2): 112-20, Jul. 2006.

Drożdż et al., "Immunoglobulin cleavage by hypochlorous acid treatment," Clinica. Chimica. acta., 236(2): 155-60, May 1995.

European Search Report in European Application No. 16849839.2 dated Feb. 18, 2019, 35 pages.

Faca et al., "Innovative proteomic approaches for cancer biomarker discovery," Biotechniques, 43(3):279-283, Sep. 2007.

Fan et al., "Identification of Niemann-Pick C1 disease biomarkers through sphingolipid profiling," J. Lipid. Res., 54(10):2800-2814, Oct. 2013.

Gadgil et al., "The LC/MS analysis of glycation of IgG molecules in sucrose containing formulations," Journal of Pharmaceutical Sciences, 96(10):2607-2621, Oct. 2007.

Gucinski et al., "Evaluation of intact mass spectrometry for the quantitative analysis of protein therapeutics," Anal. Chem., 84(18):8045-8051, Sep. 2012.

Hanash et al., "Mining the plasma proteome for cancer biomarkers," Nature, 452(7187)571-579, Apr. 2008.

Hill et al., "Serum free light chains: an alternative to the urine Bence Jones proteins screening test for monoclonal gammopathies," Clin. Chem., 52(9):1743-1748, Sep. 2006.

Holding et al., "Use of serum free light chain analysis and urine protein electrophoresis for detection of monoclonal gammopathies," Clin. Chem. Lab. Med., 49(1):83-88, Jan. 2011.

Huse et al., "Purification of antibodies by affinity chromatography," Journal of biochemical and biophysical methods, 51(3):217-31, May 2002.

Johnson et al., "Cation exchange-HPLC and mass spectrometry reveal C-terminal amidation of an IgG1 heavy chain," Anal. Biochem., 360(1):75-83, Jan. 2007.

Kalaga et al., "Unexpected presence of polyreactive catalytic antibodies in IgG from unimmunized donors and decreased levels in rheumatoid arthritis," J. Immunol., 155(5):2695-2702, Sep. 1995.

Kaplan et al., "Immunoglobulin free light chain dimers in human diseases," The Scientific World Journal, 11:726-735, Mar. 2011.

Kaplan et al., "Isolation and biochemical characterization of plasma monoclonal free light chains in amyloidosis and multiple myeloma: a pilot study of intact and truncated forms of light chains and their charge properties," Clin. Chem. Lab. Med., 46(3):335-341, Mar. 2008.

Kleennann et al., "Characterization of IgG1 immunoglobulins and peptide-Fc fusion proteins by limited proteolysis in conjunction with LC-MS," Analytical Chemistry, 80(6):2001-2009, Mar. 2008.

Kragten et al., "Site-specific analysis of the N-glycans on murine polymeric immunoglobulin A using liquid chromatography/electrospray mass spectrometry," Journal of Mass Spectrometry, 30(12): 1679-86, Dec. 1995.

(56) References Cited

OTHER PUBLICATIONS

Kyle et al., "Criteria for the classification of monoclonal gammopathies, multiple myeloma and related disorders: a report of the International Myeloma Working Group," Br. J. Haematol., 121(5):749-757, Jun. 2003.

Legros et al., "Characterization of an anti-Borrelia burgdorferi OspA conformational epitope by limited proteolysis of monoclonal antibody-bound antigen and mass spectrometric peptide mapping," Protein Science, 9(5):1002-10, May 2000.

Leung et al., "A novel and rapid approach to protein expression profiling of cerebrospinal fluid (CSF) from medulloblastoma patients using functionalized magnetic beads, AnchorChipTM technology, MALDI-TOF and MALDI-TOF/TOF mass spectrometry," 33rd Meeting of the Society of Neuroscience, 751.3, Nov. 2003.

Marien et al., "Detection of monoclonal proteins in sera by capillary zone electrophoresis and free light chain measurements," Clin. Chem., 48(9): 1600-1601, Sep. 2002.

Mazur et al., "A platform for characterizing therapeutic monoclonal antibody breakdown products by 2D chromatography and top-down mass spectrometry," The AAPS journal, 14(3):530-41, Sep. 2012.

Micallef, J. et al, Journal of Hematology & Oncology 2010, 3, 11 pages.

Mills et al., "Using mass spectrometry to quantify rituximab and perform individualized immunoglobulin phenotyping in ANCA-associated vasculitis," Analytical chemistry, 88(12):6317-25, Jun. 2016.

Minnura et al., "Contrasting glycosylation profiles between Fab and Fc of a human IgG protein studied by electrospray ionization mass spectrometry," J. Immunol. Methods., 326(1-2): 116-26, Sep. 2007.

Mohr et al., "High-efficiency nano- and micro-HPLC—high-resolution Orbitrap-MS platform for top-down proteomics," Proteomics., 10(20):3598-3609, Oct. 2010.

Murray et al., "Characterization of immunoglobulin by mass spectrometry with applications for the clinical laboratory," Crit. Rev. Clin Lab. Sci., 50(4-5):91-102, Jul.-Oct. 2013.

Oeckl et al., "CSF concentrations of cAMP and cGMP are lower in patients with Creutzfeldt-Jakob disease but not Parkinson's disease and amyotrophic lateral sclerosis," PLoS One, 7(3):e32664, Mar. 2012.

Piehler et al., "Quantitation of serum free light chains in combination with protein electrophoresis and clinical information for diagnosing multiple myeloma in a general hospital population," Clin. Chem., 54(11):1823-1830, Nov. 2008.

Qin et al., "Development of a 'reverse capture' autoantibody microarray for studies of antigen-autoantibody profiling," Proteomics., 6(10):3199-209, May 2006.

Reid et al., "Rapid whole monoclonal antibody analysis by mass spectrometry: An ultra scale-down study of the effect of harvesting by centrifugation on the post-translational modification profile," Biotechnology and Bioengineering, 107(1):85-95, Sep. 2010.

Rosati et al., "Exploring an orbitrap analyzer for the characterization of intact antibodies by native mass spectrometry," Angew. Chem. Int. Ed. Engl., 51(52): 12992-12996, Dec. 2012.

Ruan et al., "Strategy and its implications of protein bioanalysis utilizing high-resolution mass spectrometric detection of intact protein," Anal. Chem., 83(23):8937-8944, Dec. 2011.

Stoop et al., "Quantitative MALDI-FT-ICR analysis of cerebrospinal fluid of relapsing-remitting and primary progressive multiple sclerosis patients," Multiple Sclerosis., 15(9):S83, Sep. 2009.

Sun et al., "Preparation and mass spectrometric study of egg yolk antibody (IgY) against rabies virus," Rapid communications in mass spectrometry, 15(9):708-12, May 2001.

Vrana et al., "Classification of amyloidosis by laser microdissection and mass spectrometry-based proteomic analysis in clinical biopsy specimens," Blood, 114(24):4957-4960, Dec. 2009.

Wagner-Rousset et al., "The way forward, enhanced characterization of therapeutic antibody glycosylation: comparison of three level mass spectrometry-based strategies," Journal of Chromatography B, 872(1-2):23-37, Sep. 2008.

Wang et al., "Differentiation and quantification of endogenous and recombinant-methionyl human leptin in clinical plasma samples by immunocapture/mass spectrometry," J. Pharm. Biomed. Anal., 70:440-446, Nov. 2012.

Wang et al., "Molecular basis of assembly and activation of complement component C1 in complex with immunoglobulin G1 and antigen," Molecular cell, 63(1):135-45, Jul. 2016.

Wine, Y et al. Molecular deconvolution of the monoclonal antibodies that comprise the polyclonal serum response, PNAS vol. 110, No. 8, pp. 2993-2998 (Year: 2013).

Yamazaki et al., "A proteolytic modification of AIM promotes its renal excretion," Scientific Reports, 6:38762, Dec. 2016.

Zhaoyu et al., "Alteration of DBP levels in CSF of patients with MS by proteomics analysis," Cell Mol. Neurobiol., 29(2):203-210, Mar. 2009.

Aisina and Mukhametova, "Structure and Function of Plasminogen/Plasmin System," Russian Journal of Bioorganic Chemistry, Nov. 2014, 40(6):590-605.

Attealnnannan and Levinson et al., "Understanding and Identifying monoclonal gammopathies," Clinical Chemistry, Aug. 2000, 46(8B): 1230-1238.

Hutchison et al., "The pathogenesis and diagnosis of acute kidney injury in multiple myeloma," Nature Reviews Nephrology, Jan. 2012, 8:43-51.

Kiselar et al., "Direct Identification of Protein Epitopes by Mass Spectrometry Without Immobilization of Antibody and Isolation of Antibody-Peptide Complexes," Analytical Chemistry, May 1999, 71(9): 1792-1801.

Kissel and Mendell, "Neuropathies associated with monoclonal gammopathies," Neuromuscular disorders, Jan. 1996, 6(1):3-18.

Lim et al., "Identification and Location of a Cysteinyl Post-translational Modification in an Amyloidogenic kappa1 Light Chain Protein by Electrospray Ionization and Matrix-Assisted Laser Desorption/Ionization Mass Spectrometry," Analytical Biochemistry, Aug. 2001, 295:45-56.

Markowitz, "Dysproteinemia and the Kidney," Advances in Anatomic Pathology, Jan. 2004, 11:49-63.

Mischak et al., "Urinary proteome analysis using capillary electrophoresis coupled to mass spectrometry: a powerful tool in clinical diagnosis, prognosis and therapy evaluation," Journal of Medical Biochemistry, Oct. 2009, 28(4):223-234.

Persson et al., "Development of Mass Spectrometry Based Techniques for the Identification and Determination of Compositional Variability in Recombinant Polyclonal Antibody Products," Analytical Chemistry, Sep. 2010, 82(17):7274-7282.

Roberts et al., "An Integrated Strategy for Structural Characterization of the Protein and Carbohydrate Components of Monoclonal Antibodies: Application to Anti-Respiratory Syncytial Virus Mab," Analytical Chemistry, Oct. 1995, 67(20):3613-3625.

Shaheen et al., "Multiple Myeloma and Immunosecretory Disorders: An Update," Advances in Anatomic Pathology, Jul. 2008, 15(4): 196-210.

Sikkink et al., "Biochemical and Aggregation Analysis of Bence Jones Proteins From Different Light Chain Diseases," Amyloid, Mar. 2008, 15:29-39.

Wang et al., "Structural Characterization of a Recombinant Monoclonal Antibody by Electrospray Time-Of-Flight Mass Spectrometry," Pharmaceutical Research, Aug. 2005, 22(8): 1338-1349.

Acera et al., "Changes in tear protein profile in keratoconus disease," Eye, 25(9): 1225-33, Sep. 2011.

Arai et al., "Obesity-associated autoantibody production requires AIM to retain the immunoglobulin M immune complex on follicular dendritic cells," Cell Reports, 3(4):1187-98, Apr. 2013.

Balakrishnan et al., "Differential proteomic analysis of synovial fluid from rheumatoid arthritis and osteoarthritis patients," Clin. Proteomics., 11(1):1, 2014.

Baldini et al., "Correspondence between salivary proteomic pattern and clinical course in primary Sjögren syndrome and non-Hodgkin's lymphoma: a case report," Journal of translational medicine, 9(1):188, Dec. 2011.

(56) References Cited

OTHER PUBLICATIONS

Botz et al., "Detecting monoclonal light chains in urine: micro LC-ESI-Q-TOF mass spectrometry compared to immunofixation electrophoresis," British journal of haematology, 167(3):437-8, Nov. 2014.
Chow et al., "Serum immune-related proteins are differentially expressed during hibernation in the American black bear," PLoS One, 8(6), 2013.
Cohen et al., "β-Elimination and peptide bond hydrolysis: two distinct mechanisms of human IgG1 hinge fragmentation upon storage," Journal of the American Chemical Society, 129(22):6976-7, Jun. 2007.
Cretu, "Identification and Validation of Candidate Soluble Biomarkers for Psoriatic Arthritis Using Quantitative Proteomics (Doctoral dissertation)", 2015.
Dai Y, Hu C, Huang Y, Huang HY, Liu J, Lv T. A proteomic study of peripheral blood mononuclear cells in systemic lupus erythematosus. Lupus. Sep. 2008;17(9):799-804.
Deng et al., "Plasma proteomic analysis of pancreatic cancer by 2-dimensional gel electrophoresis," Pancreas, 34(3):310-7, Apr. 2007.
Deshpande et al., "GlycoSpectrumScan: fishing glycopeptides from MS spectra of protease digests of human colostrum sIgA," Journal of proteome research, 9(2):1063-75, Feb. 2010.
Ellias et al., "Proteomic analysis of saliva identifies potential biomarkers for orthodontic tooth movement," The Scientific World Journal, 2012.
Fan et al., "A single proteolytic cleavage within the lower hinge of trastuzumab reduces immune effector function and in vivo efficacy," Breast Cancer Research, Aug. 2012, 14(4):R116.
Ghafouri et al., "Newly identified proteins in human nasal lavage fluid from non-smokers and smokers using two-dimensional gel electrophoresis and peptide mass fingerprinting," Proteomics: International Edition, 2(1): 112-20, Jan. 2002.
Goetze et al., "High-mannose glycans on the Fc region of therapeutic IgG antibodies increase serum clearance in humans," Glycobiology, 21(7):949-59, Jul. 2011.
Grazio et al., "Differential expression of proteins with heparin affinity in patients with rheumatoid and psoriatic arthritis: a preliminary study," Clin. Exp. Rheumatol., 31(5):665-671, 2013.
Hess et al., "Immunoglobulin cleavage by the *Streptococcal* cysteine protease IdeS can be detected using protein G capture and mass spectrometry," Journal of microbiological methods, Aug. 2007, 70(2):284-91.
Huang et al., "Site-specific glycosylation of secretory immunoglobulin A from human colostrum. Journal of proteome research," 14(3): 1335-49, Mar. 2015.
Iannaccone et al., "Retinal pigment epithelium and microglia express the CD5 antigen-like protein, a novel autoantigen in age-related macular degeneration," Exp Eye Res., 155:64-74, 2017.
Ito and Arata, "Proton nuclear magnetic resonance study on the dynamics of the conformation of the hinge segment of human G1 immunoglobulin," Biochemistry, Nov. 1985, 24(23):6467-74.
Kim et al., "Prediction of Response to Sorafenib in Hepatocellular Carcinoma: A Putative Marker Panel by Multiple Reaction Monitoring-Mass Spectrometry (MRM-MS)," Mol. Cell Proteomics., 16(7): 1312-132, 2017.
Koh et al., "Characterization of exosomes from body fluids of dairy cows," J. Anim. Sci., 95(9):3893-3904, 2017.
Kolialexi et al., "Plasma biomarkers for the identification of women at risk for early-onset preeclampsia," Expert Rev. Proteomics., 14(3):269-276, 2017.
Kurokawa et al., "Macrophage-derived AIM is endocytosed into adipocytes and decreases lipid droplets via inhibition of fatty acid synthase activity," Cell metabolism, 11(6):479-92, Jun. 2010.
Lee et al., "Relationship between Group-Specific Component Protein and the Development of Asthma," American journal of respiratory and critical care medicine 184(5):528-536, 2011.
Lill et al., "Microwave-assisted proteomics," Mass spectrometry reviews, 26(5):657-71, Sep. 2007.
Liu et al., "Analysis of plasma proteome from cases of the different traditional Chinese medicine syndromes in patients with chronic hepatitis B," Journal of Pharmaceutical and Biomedical Analysis, 59:173-178, 2012.
Lokamani et al., "Gelsolin and ceruloplasmin as potential predictive biomarkers for cervical cancer by 2D-DIGE proteomics analysis," Pathology & Oncology Research, 20(1): 119-29, Jan. 2014.
Mitchell et al., "Alterations in the bovine bronchoalveolar lavage proteome induced by dexamethasone," Veterinary immunology and immunopathology, 118(3-4):283-93, Aug. 2007.
Moh et al., "Site-specific N-glycosylation of recombinant pentameric and hexameric human IgM," Journal of The American Society for Mass Spectrometry, 27(7):1143-55, Apr. 2016.
Okamoto et al., "Proteome analysis of bronchoalveolar lavage fluid in chronic hypersensitivity pneumonitis," Allergology International, 61 (1):83-92, Jan. 2012.
Oruc et al., "IgA structure variations associate with immune stimulations and IgA mesangial deposition," Journal of the American Society of Nephrology, 27(9):2748-61, Sep. 2016.
Pabst et al., "A microarray-matrix-assisted laser desorption/ionization-mass spectrometry approach for site-specific protein N-glycosylation analysis, as demonstrated for human serum immunoglobulin M (IgM)," Molecular & Cellular Proteomics, 14(6): 1645-56, Jun. 2015.
Salinas et al., "Buffer-dependent fragmentation of a humanized full-length monoclonal antibody," Journal of pharmaceutical sciences, 99(7):2962-74, Jul. 2010.
Sandoval et al., "Rapid removal of N-linked oligosaccharides using microwave assisted enzyme catalyzed deglycosylation," International Journal of Mass Spectrometry, 259(1-3): 117-23, Jan. 2007.
Sanjurjo et al., "AIM/CD5L: a key protein in the control of immune homeostasis and inflammatory disease," J. Leukoc. Biol., 98(2): 173-184, Aug. 2015.
Sarrias et al., "Biochemical characterization of recombinant and circulating human Spα," Tissue antigens, Apr. 2004, 63(4):335-44.
Skriner et al., "Association of citrullinated proteins with synovial exosomes," Arthritis & Rheumatism: Official Journal of the American College of Rheumatology, Dec. 2006, 54(12):3809-14.
Sloane et al., "Proteomic analysis of sputum from adults and children with cystic fibrosis and from control subjects. American journal of respiratory and critical care medicine," Dec. 2005, 172(11): 1416-26.
Tissot et al., "IgM Are Associated to Sp Alpha (CD5 Antigen-Like)," Electrophoresis, 23(7-8): 1203-1206, Apr. 2002.
Vase et al., "A57 Proteomic profiling of pretreatment serum from HIV-infected patients identifies candidate markers predictive of lymphoma development," AIDS, 2016, 30(12):1889-1898.
Vlasak and Ionescu, 2011, mAbs 3:253-263.
Wang et al., "Discovery of potential colorectal cancer serum biomarkers through quantitative proteomics on the colonic tissue interstitial fluids from the AOM-DSS mouse model," J. Proteomics, 2016, 132:31-40.
Xu et al., "Discovery and identification of serum potential biomarkers for pulmonary tuberculosis using iTRAQ-coupled two-dimensional LC-MS/MS," Proteomics, 2014, 14(2-3):322-331.
Yin et al., "Protein biomarkers of new-onset cardiovascular disease: prospective study from the systems approach to biomarker research in cardiovascular disease initiative," Arterioscler. Thromb. Vasc. Biol., 2014, 34(4):939-945.
Zhang et al., "Proteomic analysis of plasma in adult active pulmonary tuberculosis patients with diabetes mellitus," The FASEB Journal, Apr. 2015, 29(1_supplement):275-7.
Zhong et al., "Microwave-assisted acid hydrolysis of proteins combined with liquid chromatography MALDI MS/MS for protein identification," Journal of the American Society for Mass Spectrometry, Apr. 2005, 16(4):471-81.
Zhong et al., "Protein sequencing by mass analysis of polypeptide ladders after controlled protein hydrolysis," Nature biotechnology, Oct. 2004, 22(10): 1291-6.
Zhou et al., "Quantitative analysis of N-linked glycoproteins in tear fluid of climatic droplet keratopathy by glycopeptide capture and iTRAQ," Journal of proteome research, Apr. 2009, 8(4): 1992-2003.

(56) References Cited

OTHER PUBLICATIONS

VanDuijn et al., "Quantitative measurement of immunoglobulins and free light chains using mass spectrometry," Analytical chemistry, 87(16):8268-74, Aug. 2015.

* cited by examiner

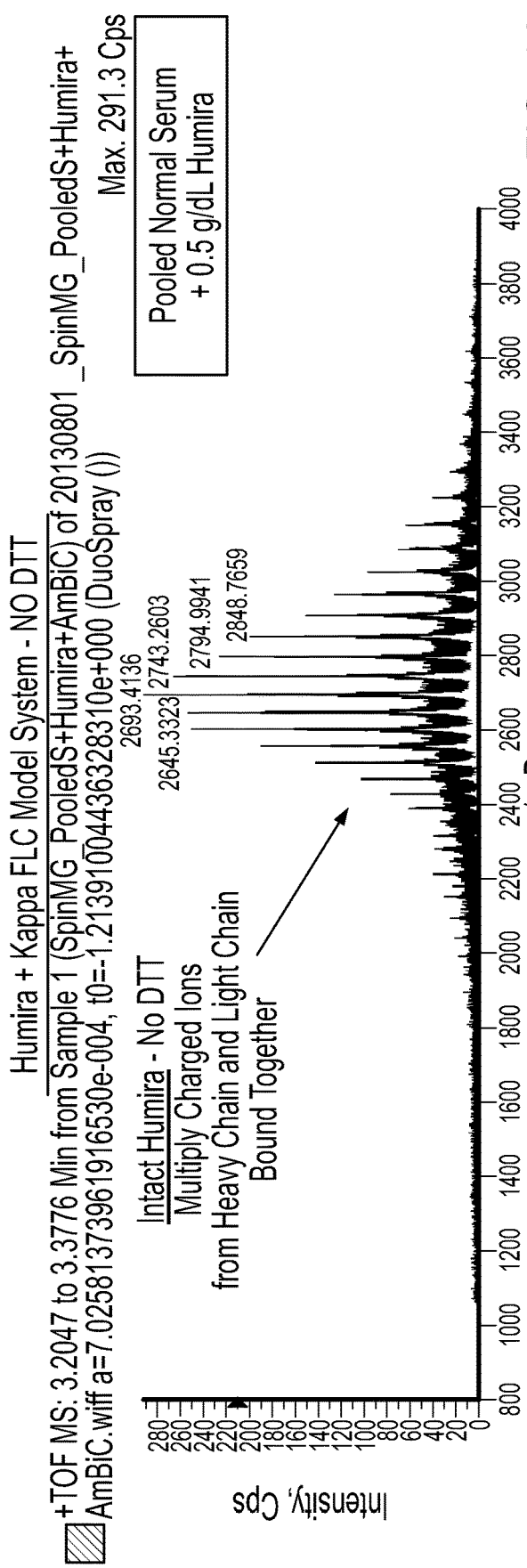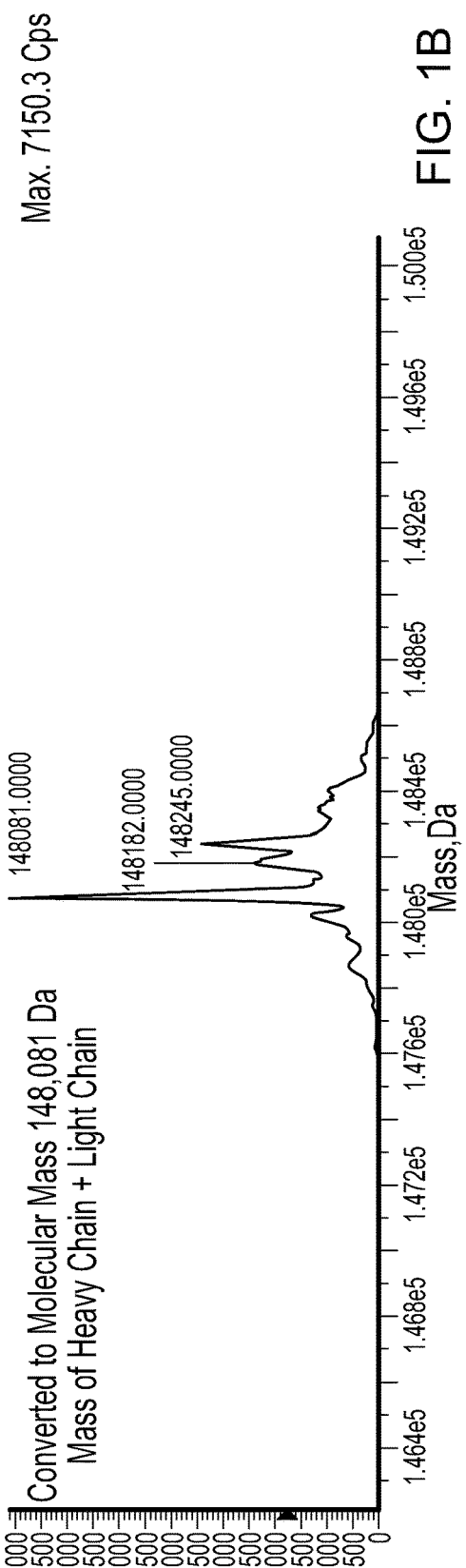
FIG. 1A
FIG. 1B

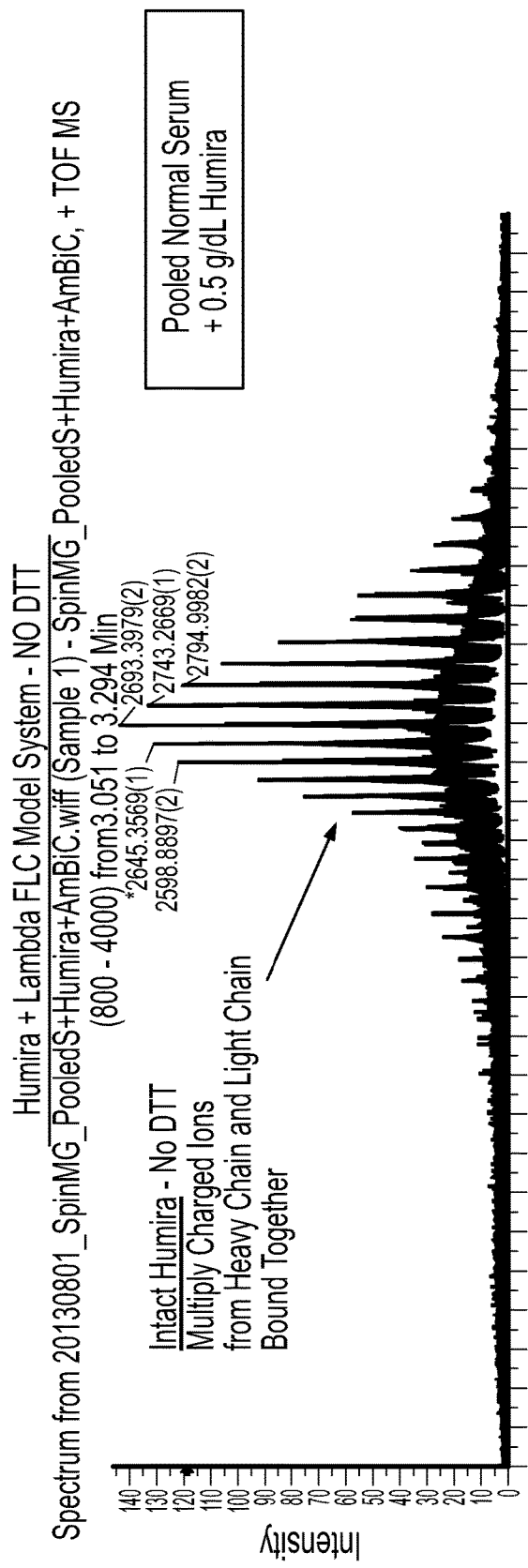
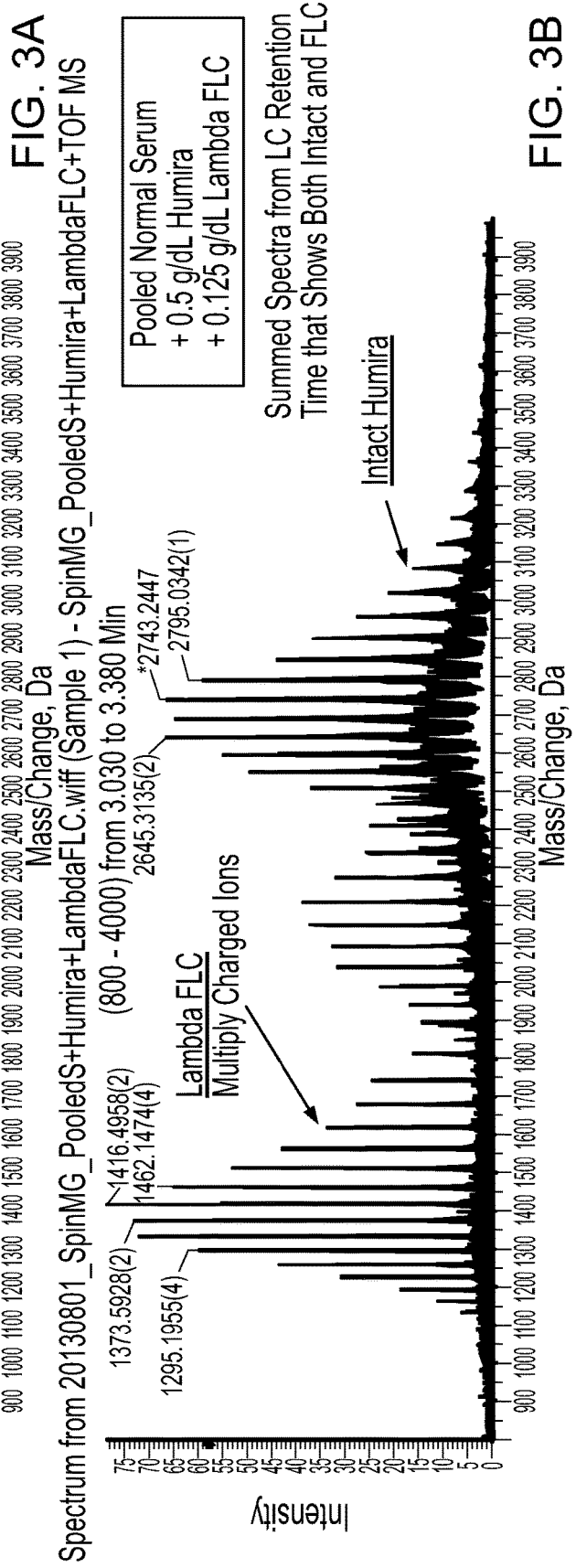
FIG. 3A
FIG. 3B

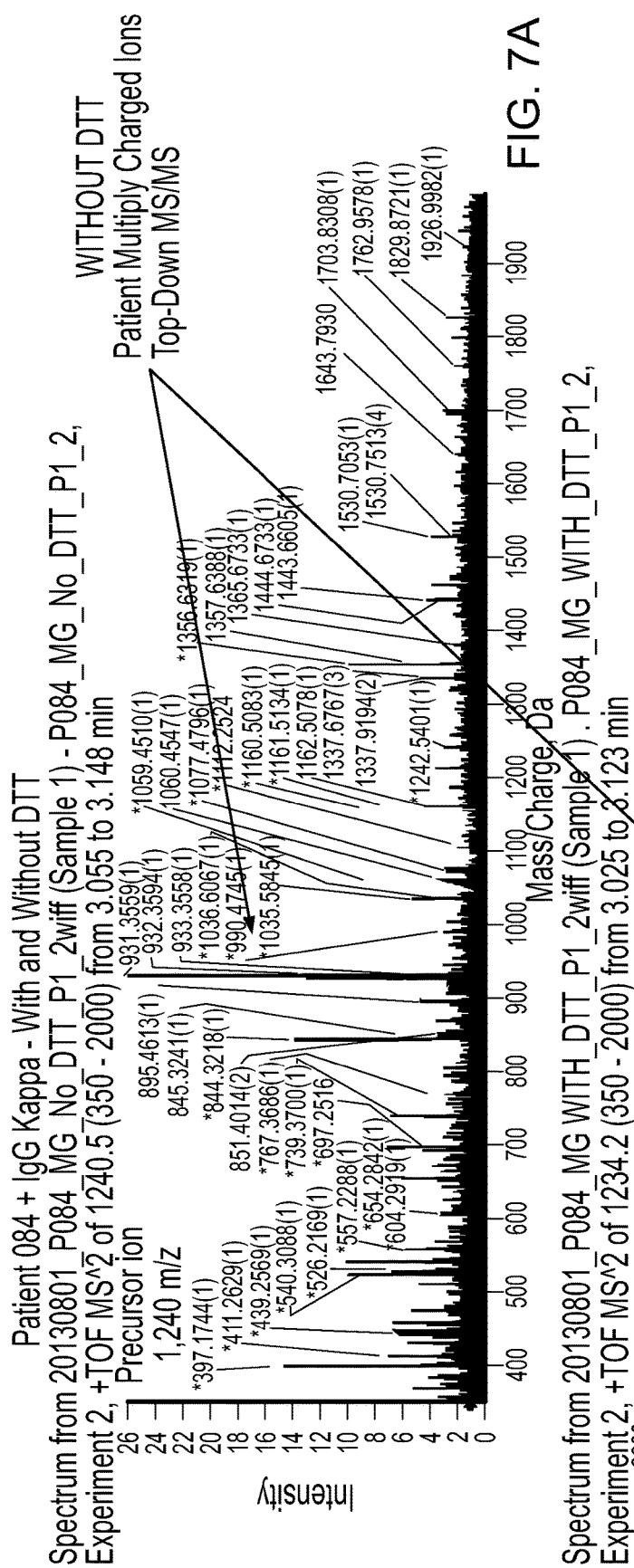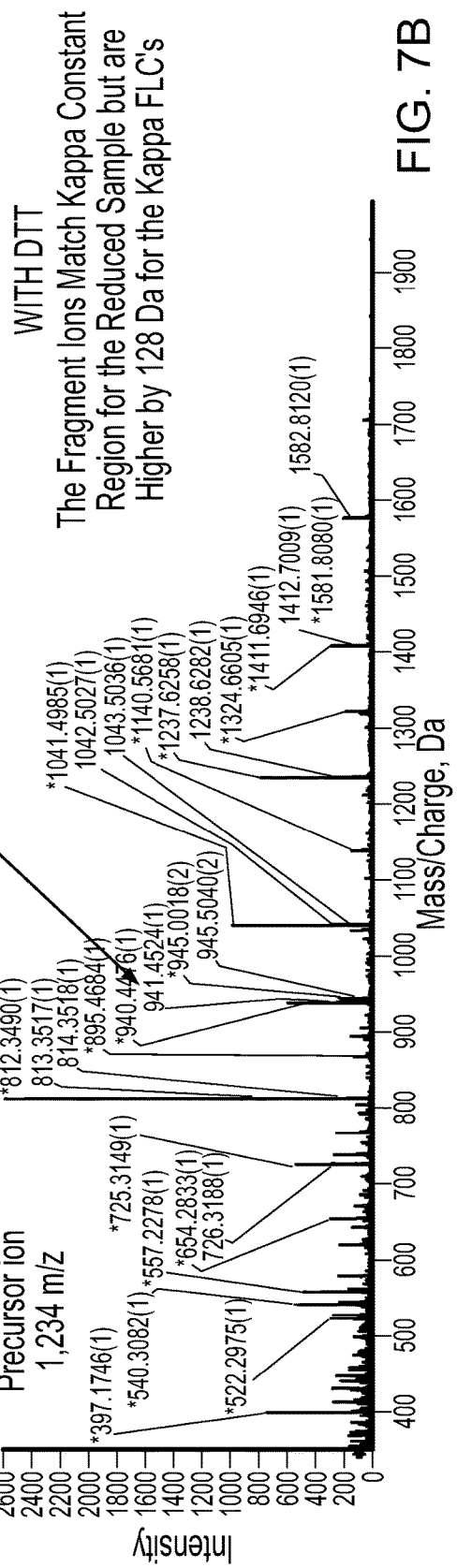
FIG. 7A
FIG. 7B

IDENTIFICATION OF IMMUNOGLOBULIN FREE LIGHT CHAINS BY MASS SPECTROMETRY

CROSS-REFERENCE TO RELATED APPLICATIONS

This application is a National Stage application under 35 U.S.C. § 371 of International Application No. PCT/US2016/053675, having an International Filing Date of Sep. 26, 2016, which claims priority to U.S. Provisional Application Ser. No. 62/232,182, filed on Sep. 24, 2015, the contents of which are incorporated by reference in their entirety.

TECHNICAL FIELD

This document relates to methods for identifying one or more immunoglobulin free light chains in a sample using mass spectrometry.

BACKGROUND

Immunoglobulins (Igs) have a two-fold symmetry with each intact Ig containing two heavy and two light chains. The light chains are subdivided into two main types (kappa and lambda) based on their amino acid sequences in the C terminal constant region. Plasma cells are responsible for synthesis of the heavy and light chains resulting in the production of an intact Ig.

The amino acid sequence of a human immunoglobulin light chain consists of three regions: the N-terminal V region (approximately 107 amino acids for kappa and 110 amino acids for lambda), the J region (12 amino acids), and the C-terminal C region (106 amino acids). Each region is translated from a specific set of genes expressed only in B cells which make and secrete light chains either as part of an intact immunoglobulin or as a free light chain. B-cells are also able to randomly mutate V and J region genes for light chains through the process of somatic hypermutation resulting in a large number of different gene combinations (approximately $1.3 \times 10^3$ for kappa alone) (see, e.g., Lefranc, M P. *Cold Spring Harb Protoc* 2011; 2011:595-603). Since the light chain V and J region gene sequences are created randomly, the Central Limit Theorem (Mukhopadhyay, N and Chattopadhyay, B. *Sequential Anal* 2012; 31:265-77) predicts that the amino acid sequence of the expressed light chain repertoire should have a normally distributed molecular mass profile.

SUMMARY

Provided herein is a method for identifying one or more immunoglobulin free light chains in a sample. The method includes (a) providing a sample; (b) subjecting the sample to a mass spectrometry technique to obtain a mass spectrum of the sample; and identifying the presence of the one or more immunoglobulin free light chains.

In some embodiments, the sample is suspected to include an immunoglobulin free light chain.

In some embodiments, the one or more immunoglobulin free light chains are selected from the group consisting of free kappa light chains and free lambda light chains, and mixtures thereof. For example, the immunoglobulin free light chain can be a free kappa light chain. Additionally, the method can include identifying at least two free kappa light chains. In some embodiments, the immunoglobulin free light chain is a free lambda light chain. For example, the method can include identifying at least two free lambda light chains.

In some embodiments, the one or more immunoglobulin free light chains includes at least one of a glycosylated immunoglobulin free light chain, a cysteinylated immunoglobulin free light chain, and a glutathionylated immunoglobulin free light chain.

In some embodiments, identifying the one or more immunoglobulin free light chains occurs in the presence of a polyclonal background.

In some embodiments, the method further includes measuring the concentration of the one or more immunoglobulin free light chains in the sample.

In some embodiments, the method has a peak area percent variation of less than about 15% when the concentration of at least one immunoglobulin free light chain in the sample is measured 5 to 15 times. For example, the method can have a peak area percent variation of less than about 10% when the concentration of at least one immunoglobulin free light chain in the sample is measured 5 to 15 times.

In some embodiments, the method further includes identifying at least one immunoglobulin free light chain dimer.

In some embodiments, the method further includes contacting the sample with a reducing agent prior to subjecting the sample to the mass spectrometry technique. The reducing agent can be selected from the group consisting of dithiothreitol (DTT), reduced glutathione, (3-mercaptoethanol, tris(2-carboxyethyl) phosphine hydrochloride, cysteine, 2-mercaptoethylamine, 3-mercaptopropionic acid, and mixtures thereof. In some embodiments, the reducing agent is dithiothreitol.

In some embodiments, the method does not include contacting the sample with a reducing agent.

In some embodiments, the method does not include purifying the sample.

In some embodiments, the mass spectrometry technique is LC-MS/MS. The LC-MS/MS technique can include a quadrupole time-of-flight mass spectrometer. In some embodiments, the mass spectrometry technique is a top-down mass spectrometry technique.

In some embodiments, the sample is a serum sample, a urine sample, a cerebrospinal fluid sample, or whole blood.

In some embodiments, the sample is from a single subject and the method further includes diagnosing a disorder in the subject wherein the disorder is a plasma cell dyscrasia. For example, the sample can be from a single subject and the method can further include diagnosing at least one of a multiple myeloma or a light chain amyloidosis.

In some embodiments, the sample is from a subject and the method further comprises diagnosing a disorder in the subject wherein the disorder is at least one of multiple myeloma, monoclonal gammopathy of undetermined significance, B-cell chronic lymphocytic leukemia, Waldenstroms macrogloblinemia, amyloid light chain amyloidosis, or non-secretory myeloma.

In some embodiments, the sample is from a subject and the method further comprises distinguishing an auto-immune response from a monoclonal gammopathy in the subject.

Also provided herein is a method for identifying one or more immunoglobulin free light chains in a sample that includes (a) providing a sample; (b) contacting the sample with a reducing agent; (c) subjecting the sample to a mass spectrometry technique to obtain a mass spectrum of the sample; and (d) identifying the presence or absence of one or more immunoglobulin free light chains.

Additionally, provided herein is a method for diagnosing a disorder in a subject. The method includes (a) providing a sample from the subject; (b) subjecting the sample to a mass spectrometry technique to obtain a mass spectrum of the sample; and (c) identifying the presence or absence of one or more immunoglobulin free light chains.

In some embodiments, the disorder is selected from multiple myeloma, monoclonal gammopathy of undetermined significance, B-cell chronic lymphocytic leukemia, Waldenstroms macrogloblinemia, amyloid light chain amyloidosis, non-secretory myeloma and combinations thereof.

In some embodiments, the sample is a serum sample, a urine sample, a cerebrospinal fluid sample, or whole blood.

In some embodiments, after diagnosing the subject as having a disorder, the method further includes administering to the subject a therapeutically effective amount of a therapeutic agent to treat the disorder. The therapeutic agent can include one or more of chlorambucil, fludarabine, cyclophosphamide, rituximab, bendamustine, carfilzomib, cyclophosphamide, doxorubicin, vincristine, prednisone, chlorambucil, obinutuzumab, ofatumumab, pentostatin, alemtuzumab, fludarabine, bortezomib, thalidomide, dexamethasone, doxorubicin, ibrutinib, melphalan, adriamycin, lenalidomide, pomalidomide, a bisphosphonate, a glycosaminoglycans, a purine nucleoside analog, and a monoclonal antibody.

In some embodiments, the disorder is monoclonal gammopathy of undetermined significance and the therapeutic agent is a bisphosphonates.

In some embodiments, the disorder is B-cell chronic lymphocytic leukemia and the therapeutic agent is selected from chlorambucil, fludarabine, cyclophosphamide, rituximab, bendamustine, cyclophosphamide, doxorubicin, vincristine, prednisonea, chlorambucil, obinutuzumab, or ofatumumab, pentostatin, alemtuzumab, fludarabine, monoclonal antibody, and combinations thereof.

In some embodiments, the disorder is Waldenstroms macrogloblinemia and the therapeutic agent is selected from bortezomib, thalidomide, fludarabine, dexamethasone, chlorambucil, rituximab, cyclophosphamide, doxorubicin, vincristine, prednisone, a monoclonal antibody, a purine nucleoside analog, ibrutinib, and combinations thereof.

In some embodiments, the disorder is amyloid light chain amyloidosis and the therapeutic agent is selected from a melphalan, prednisone, vincristine, adriamycin, dexamethasone, bendamustine, thalidomide, cyclophosphamide, lenalidomide, pomalidomide, bortezomib, a glycosaminoglycans, and combinations thereof.

In some embodiments, the disorder is non-secretory myeloma and the therapeutic agent is selected from thalidomide, bortezomib, lenalidomide, carfilzomib, pomalidomide and combinations thereof.

Also, provided herein is a method for diagnosing a monoclonal gammopathy in a subject. The includes: (a) providing a sample from the subject; (b) subjecting the sample to a mass spectrometry technique to obtain a mass spectrum of the sample; and (c) diagnosing a monoclonal gammopathy in the subject based on the identification of one or more free kappa immunoglobulin light chains or one or more free lambda immunoglobulin light chains.

In some embodiments, the method further includes contacting the sample comprising an immunoglobulin free light chain with a reducing agent prior to subjecting the sample to the mass spectrometry technique.

Additionally, provided herein is a method for monitoring a treatment of a monoclonal gammopathy in a subject. The method includes: (a) providing a first sample of the subject, obtained before the treatment; (b) providing a second sample of the subject obtained during or after the treatment; (c) subjecting the first and second samples to a mass spectrometry technique to obtain a mass spectrum of the first and second samples; (d) determining the concentration of at least one of free kappa immunoglobulin light chain or at least one free lambda immunoglobulin light chain in the first and second samples; and (e) comparing the concentration of the at least one free kappa immunoglobulin light chain or the at least one free lambda immunoglobulin light chain in the first and second samples.

In some embodiments, the method further includes contacting the first and second samples comprising an immunoglobulin free light chain with a reducing agent prior to subjecting the first and second samples to the mass spectrometry technique.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Shows the LC-MS/MS spectra (non-deconvoluted, FIG. 1A and deconvoluted, FIG. 1B), for normal serum spiked with HUMIRA®. FIG. 1A shows the non-deconvoluted LC-MS/MS spectra for normal serum spiked with HUMIRA®. FIG. 1B shows the deconvoluted LC-MS/MS spectra for normal serum spiked with HUMIRA®

FIG. 2. Shows the LC-MS/MS spectra of normal serum spiked with both kappa free light chains and HUMIRA®.

FIG. 3. Shows the LC-MS/MS spectra for normal serum spiked with both lambda free light chains and HUMIRA®. FIG. 3A shows the LC-MS/MS spectra for normal serum spiked with HUMIRA®. FIG. 3B shows the LC-MS/MS spectra for normal serum spiked with both lambda free light chains and HUMIRA®.

FIG. 4. Shows the LC-MS/MS spectra for normal serum spiked with both lambda free light chains and HUMIRA® and shows the presence of an immunoglobulin free light chain dimer.

FIG. 7. Shows the top down mass spectrometry spectra for serum taken from a patient diagnosed with monoclonal gammopathy of undetermined significance. FIG. 7A shows the top down mass spectrometry spectra for serum, which has not been treated with dithiothreitol, taken from a patient diagnosed with monoclonal gammopathy of undetermined significance. FIG. 7B shows the top down mass spectrometry spectra for serum, which has been treated with dithiothreitol, taken from a patient diagnosed with monoclonal gammopathy of undetermined significance FIG. 8. Shows the LC-MS/MS spectra for serum taken from a patient diagnosed with smoldering myeloma.

FIG. 9A shows multiply charged ions from the kappa FLC monomer along with its retention time and molecular mass determined by deconvolution of the mass spectrum; (ii) FIG. 9B shows multiply charged ions from the kappa FLC dimer along with its retention time and molecular mass determined by deconvolution of the mass spectrum; and (iii) FIG. 9C shows multiply charged ions from adalimumab (heavy chain and light chain intact) along with its retention time and molecular mass determined by deconvolution of the mass spectrum.

FIG. 10A is from control serum from a healthy donor. FIG. 10B is from an AL patient. The numbered peaks represent signal from high abundance proteins that are not completely removed by MELON™ GEL, which are presumed to be; 1—(alpha-1-antitrypsin), 2 (transferrin), and 3, an unknown 61 kDa protein. Signal presumed to be from an FLC dimer in the AL patient serum is labeled in TIC B.

DETAILED DESCRIPTION

Figure 2A:
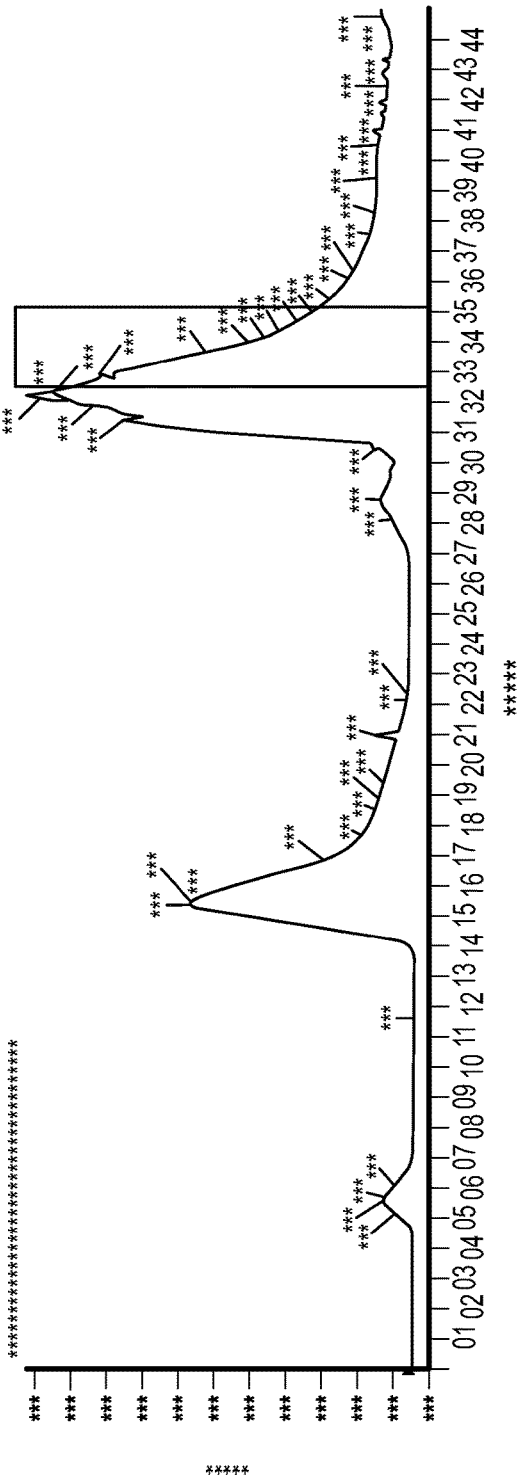
FIG. 2A shows the retention times for the LC-MS/MS spectra of normal serum spiked with both kappa free light chains and HUMIRA®.

Normal plasma cells produce excess kappa and light chains which are excreted into serum (free light chains, FLC). Approximately twice as many kappa to lambda light chains are produced in humans. Each FLC molecule contains approximately 220 amino acids and each molecule is composed of an N-terminal domain that contains the variable (VL) region and a C-terminal domain that contains the constant (CL) region. This methods described herein utilize the unique mass of the VL region as a marker of plasma cell clonality.

Plasma cell immunoglobulin production involves the matching of a light chain (LC) with a heavy chain (HC) via a disulfide bond. The HC-LC dimer is then coupled to another HC-LC dimer through additional disulfide bonds to form an immunoglobulin that is secreted from the cell. During normal immunoglobulin production plasma cells produce excess polyclonal free light chains (FLC) that are secreted into circulation and in healthy individuals these excess FLC are reabsorbed and metabolized in the kidney. However, individuals with a plasmaproliferative disorder have a population of clonal plasma cells that secrete a monoclonal FLC into circulation at a concentration higher than the normal polyclonal LC repertoire. A clinical application of serum FLC measurements are for patients with monoclonal gammopathies. In these diseases, a dysregulated or malignant plasma cell clone, or clones, overproduce Igs and FLCs in comparison to the normal polyclonal background, which can be detected by skewed kappa/lambda FLC ratios or by quantitation of an Ig in excess of the poly clonal background.

Currently in clinical medicine, FLC ratios are measured by immunoassays that rely on specific antibodies, which bind to antigenic sites in the FLC. However, current methods are not specific for individual kappa and lambda FLCs and, hence, quantitation of these groups includes the polyclonal background. Accordingly, monoclonality must be inferred from the kappa/lambda ratio. Unfortunately, the reliance on kappa/lambda ratios can be affected by other conditions occurring in the patient. For example, patients who have autoimmune disease may have skewed polyclonal kappa and lambda ratios independent of or in addition to a monoclonal gammopathy.

The methods described herein utilize high mass accuracy to measure FLCs in serum, urine, cerebrospinal fluid (CSF), and other body fluids. The mass accuracy allows for direct quantitation of each kappa and lambda light chain. Thus, a reliance on kappa and lambda ratios alone are not necessary to infer monoclonality.

Provided herein is a method for identifying one or more immunoglobulin free light chains in a sample. The method includes (a) providing a sample; (b) subjecting the sample to a mass spectrometry technique to obtain a mass spectrum of the sample; and identifying the presence or absence of the one or more immunoglobulin free light chains.

As used herein, the term "immunoglobulin free light chains" refers to the excess kappa and lambda light chains that are excreted from plasma cells into serum (free light chains, FLC). Immunoglobulin free light chains can also refer to dimers of immunoglobulin free light chains.

In some embodiments, the sample is suspected to include an immunoglobulin free light chain.

In some embodiments, the one or more immunoglobulin free light chains are selected from the group consisting of free kappa light chains, free lambda light chains, and mixtures thereof. For example, the immunoglobulin free light chain can be a free kappa light chain. Additionally, the method can include identifying at least two free kappa light chains (i.e. kappa light chains having distinct mass or mass to charge ratios). In some embodiments, the immunoglobulin free light chain is a free lambda light chain. Additionally, the method can include identifying at least two free lambda light chains (i.e. lambda light chains having distinct mass or mass to charge ratios).

In some embodiments, the one or more immunoglobulin free light chains include at least one of a glycosylated immunoglobulin free light chain, a cysteinylated immunoglobulin free light chain, and a glutathionylated immunoglobulin free light chain. For example, the one or more immunoglobulin free light chains can include at least one of a glycosylated immunoglobulin free light chain and a cysteinylated immunoglobulin free light chain. A cysteinylated immunoglobulin free light chain can be identified based on the difference between the mass observed for the immunoglobulin free light chain and the mass calculated for the immunoglobulin free light chain. For example a difference of about 119 Daltons (Da) between the mass observed for the immunoglobulin free light chain and the mass calculated for the immunoglobulin free light chain can indicate the presence of a cysteinylated immunoglobulin free light chain. Similarly, a glutathionylated immunoglobulin free light chain can be identified if the difference between the mass observed for the immunoglobulin free light chain and the mass calculated for the immunoglobulin free light chain. For example, a difference of about 305 Da, which is equal to the mass of a glutathione addition to a cysteine residue, between the mass observed for the immunoglobulin free light chain and the mass calculated for the immunoglobulin free light chain can indicate the presence of a glutathionylated immunoglobulin free light chain.

Figure 17:
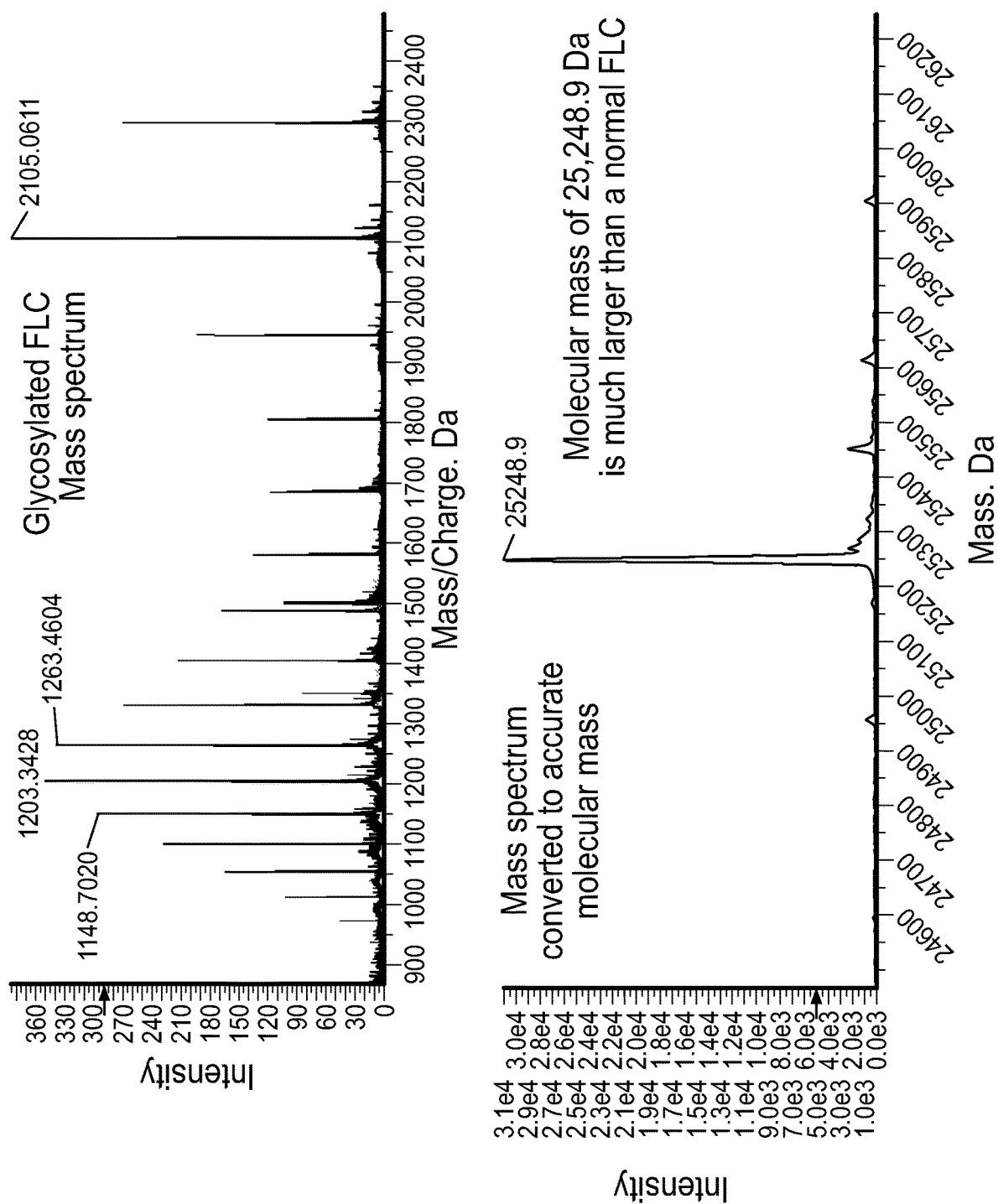
FIG. 17. Shows a mass spectrum showing the FLC lambda monomer multiply charged ions from a patient sample including glycosylated FLCs (top). The inset shows the molecular mass of the glycosylated light chain after deconvolution.
Figure 18:
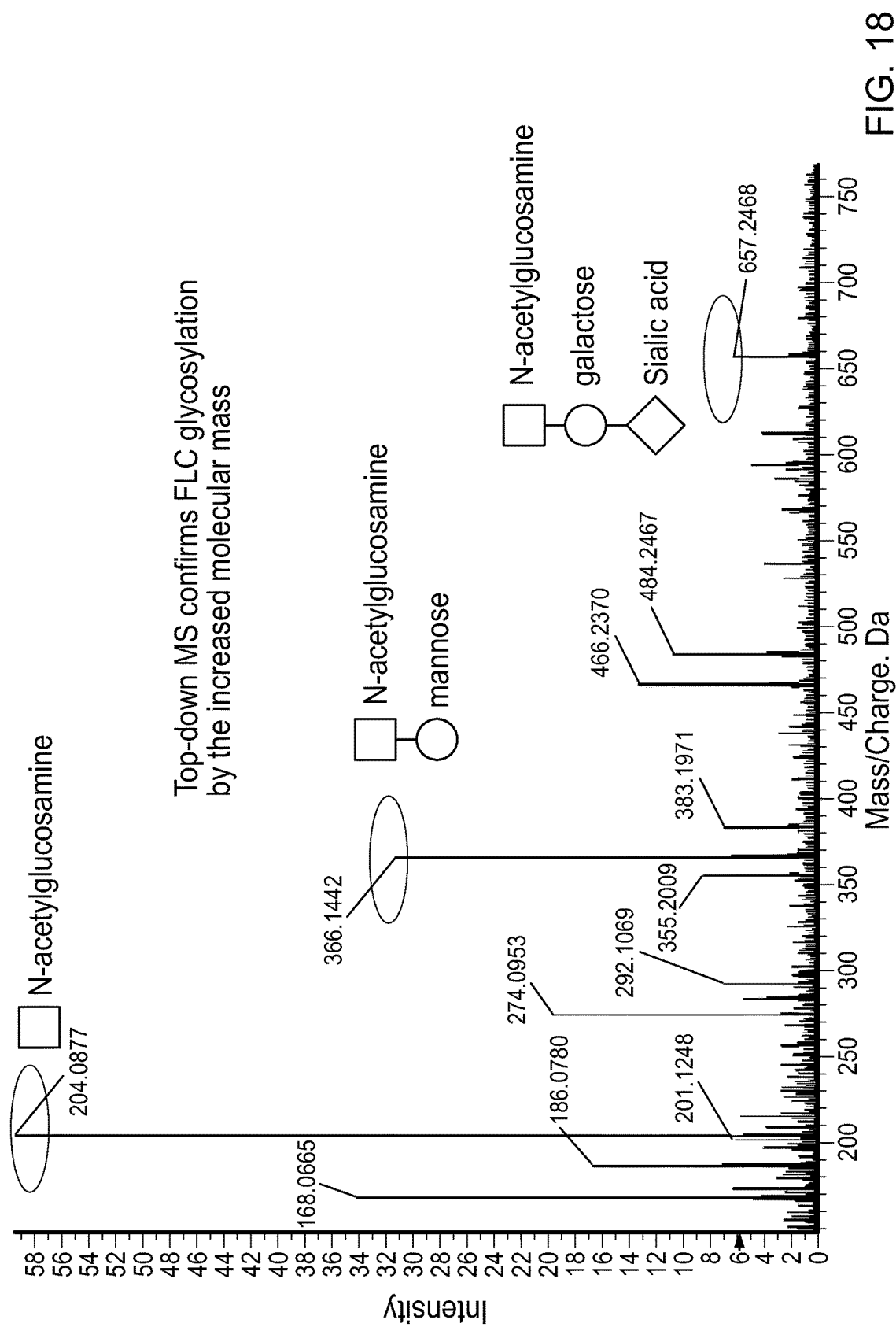
FIG. 18. Shows a top-down MS fragment ion mass spectrum showing detection and confirmation of glycosylation of FLCs.

Exemplary scans of a sample containing glycosylated immunoglobulin free light chains using the methods described herein is show in FIGS. 17 and 18.

In some embodiments, the identifying the one or more immunoglobulin free light chains occurs in the presence of a polyclonal background.

In some embodiments, the method further includes measuring the concentration of the one or more immunoglobulin free light chains in the sample. For example, the concentration of the one or more immunoglobulin free light chains can be measured by examining the peak area of the resulting mass spectrometry spectrum and comparing this to a standardized curve. In some embodiments, an internal sample can be included in or added to the sample.

In some embodiments, the method has a peak area percent variation of less than about 15% when the concentration of at least one immunoglobulin free light chain in the sample is measured 5 to 15 times. For example, the method can have a peak area percent variation of less than about 10% when the concentration of at least one immunoglobulin free light chain in the sample is measured 5 to 15 times.

In some embodiments, the method further includes-identifying at least one immunoglobulin free light chain dimer. For example, a kappa free light chain dimer or a lambda free light chain dimer.

In some embodiments, the method further includes contacting the sample with a reducing agent prior to subjecting the sample to the mass spectrometry technique. The immunoglobulin light chains can be decoupled from immunoglobulin heavy chains by cleavage of the disulfide bonds between the light and heavy chains. Additionally, the reducing agent can decouple immunoglobulin free light chain dimers by reducing disulfide bonds. The reducing agent can be selected from the group consisting of dithiothreitol (DTT), reduced glutathione, (3-mercaptoethanol, tris(2-carboxyethyl) phosphine hydrochloride, cysteine, 2-mercaptoethylamine, 3-mercaptopropionic acid, and mixtures thereof. In some embodiments, the reducing agent is dithiothreitol.

In some embodiments, the method does not include contacting the sample with a reducing agent.

In some embodiments, the method does not include purifying the sample prior to subjecting the sample to a mass spectrometry technique. For example, in some embodiments, the method does not include immunopurifying the sample prior to subjecting the sample to the mass spectrometry technique. Similarly, in some embodiments, the method does not include performing chromatography on the sample prior to subjecting the sample to the mass spectrometry technique. In some embodiments, the method does not include purifying the sample (e.g., immunopurification) prior to subjecting the sample to the mass spectrometry technique but does include centrifuging the sample prior to subjecting the sample to the mass spectrometry technique. In some embodiments, the method does not include immunopurification prior to subjecting the sample to the mass spectrometry technique. In some embodiments, the method includes immunopurification with antibodies (e.g., antibodies specific for immunoglobulin free light chains). In some embodiments, the method includes purification using a MELON™ GEL.

In some embodiments, prior to subjecting the sample to the mass spectrometry technique, the sample can be purified by affinity purification, (e.g., MELON™ GEL purification, such as mixing the sample with MELON™ GEL beads). Further, the method can include contacting the sample with a non-reducing buffer (e.g., ammonium bicarbonate) prior to subjecting the sample to the mass spectrometry technique.

In some embodiments, the mass spectrometry technique is LC-MS/MS. The LC-MS/MS technique can include a quadrupole time-of-flight mass spectrometer. A quadrupole mass analyzer (Q) consists of four cylindrical rods, set parallel to each other. In a quadrupole mass spectrometer, the quadrupole is the component of the instrument responsible for filtering sample ions based on their mass-to-charge ratio (m/z). The time-of-flight (TOF) analyzer uses an electric field to accelerate the ions through the same potential, and then measures the time they take to reach the detector. If the particles all have the same charge, the kinetic energies are identical, and their velocities depend only on their masses. Lighter ions reach the detector first. Any ESI-Q-TOF mass spectrometer can be used, e.g., the ABSciex TripleTOF 5600 quadrupole time-of-flight mass spectrometer. The mass spectrum, e.g., the mass spectrum of multiply charged intact light chain or heavy chain polypeptide ions, can be analyzed to identify one or more peaks at an appropriate mass/charge expected for the chain. For example, for the light chains, the peaks can occur at about 600-2700 m/z, 700-2400 m/z, 800-2100 m/z, 900-1800 m/z, 1000-1600 m/z, or about 1000-1500 m/z. In some embodiments, the peaks can occur at about 600-2500 m/z. Fragment ion peaks can be detected at a range of m/z of 250-2000. In some embodiments, at least one of a +11 and a +18 charge state is used for a immunoglobulin free light chain monomer. For example, the peak area from an extracted ion chromatogram (EIC) generated using the +18 charge state for the immunoglobulin free light chain monomer can be used to calculate the % CV values. In some embodiments, at least one of a +33 and a +36 charge state is used for an immunoglobulin free light chain dimer. For example, the peak area from an extracted ion chromatogram (EIC) generated using the +36 charge state for the immunoglobulin free light chain dimer can be used to calculate the % CV values.

In some embodiments, the source conditions include an IS (ion spray voltage) of about 4500 volts (V) to about 6500 V or about 5000 V to 6000 V, or about 4500 V, 5000 V, 5500 V, 6000 V, or about 6500 V. For example, the source conditions can include an IS of about 5500 V.

In some embodiments the source conditions include a temperature of about 350° C. to about 650° C., about 400° C. to about 600° C., about 450° C. to about 550° C., or about 475° C. to about 525° C., or about 350° C., 400° C., 450° C., 475° C., 500° C., 525° C., 550° C., 600° C., or about 650° C. For example, the source conditions can include a temperature of about 500° C.

In some embodiments the source conditions include a curtain gas flow (CUR) of about 35 to about 55, or about 40 to about 50, or about 35, 40, 45, 50, or about 55. For example, the source conditions can include a curtain pressure (CUR) of about 45.

In some embodiments the source conditions include an ion source gas 1 (GS1) of about 25 to about 45 or about 30 to about 40, or about 25, 30, 35, 40, or about 45. For example, the source conditions can include an ion source gas 1 (GS1) of about 35.

In some embodiments the source conditions include an ion source gas 2 (GS2) of about 20 about 40 or about 25 to about 35, or about 20, 25, 30, 35, or about 40. For example, the source conditions can include an ion source gas 2 (GS2) of about 30.

In some embodiments the source conditions include a collision energy (CE) (e.g., the potential drop across the collision cell) of 30±5, 40±5, 50±5, 60±5, or 70 50±5. For example, the source conditions can include a CE of 50±5.

In some embodiments the source conditions include an IS of about 5500, a temperature of about 500° C., a CUR of about 45 psi, a GS1 of about 35 psi, a GS2 of about 30 psi, and a CE of 50±5.

In some embodiments, the mass spectrometry technique is a top-down mass spectrometry technique. For example, when a top-down mass spectrometry technique is used the method can include identifying the isotype of an immunoglobulin free light chain.

Additional mass spectrometry techniques are described in PCT/US2015/24379 and PCT/US2014/022475, each of which is incorporated by reference in its entirety.

In some embodiments, the sample is from a single subject and the method further includes diagnosing a disorder in the subject wherein the disorder is a plasma cell dyscrasia. For example, the sample can be from a single subject and the method can further include diagnosing at least one of a multiple myeloma or a light chain amyloidosis.

In some embodiments, the sample is a serum sample, a urine sample, a cerebrospinal fluid sample, or a whole blood sample.

In some embodiments, the sample is from a single subject and the method further comprises diagnosing a disorder in the subject wherein the disorder is at least one of monoclonal gammopathy of undetermined significance, B-cell chronic lymphocytic leukemia, Waldenstrom macrogloblinemia, amyloid light chain amyloidosis, or non-secretory myeloma.

In normal serum samples the free kappa light chains can have a range, 3.3-19.4 mg/L and the free lambda light chains can have a range of 5.7-26.3 mg/L. See, e.g., *Clin Chem.* 2002 September; 48(9) pages 1437-44.

In some embodiments, the sample is from a single subject and the method further comprises distinguishing an auto-immune response from a monoclonal gammopathy in the subject.

Also provided here in is a method for identifying one or more immunoglobulin free light chains in a sample that includes (a) providing a sample; (b) contacting the sample with a reducing agent; (c) subjecting the sample to a mass spectrometry technique to obtain a mass spectrum of the sample; and (d) identifying the presence or absence of one or more immunoglobulin free light chains.

Additionally, provided herein is a method for diagnosing a disorder in a subject. The method includes (a) providing a sample from the subject; (b) subjecting the sample to a mass spectrometry technique to obtain a mass spectrum of the sample; and (c) identifying the presence or absence of one or more immunoglobulin free light chain.

In some embodiments, the disorder is a monoclonal gammopathy. In some embodiments, the disorder is selected from multiple myeloma, monoclonal gammopathy of undetermined significance, B-cell chronic lymphocytic leukemia, Waldenstrom's macrogloblinemia, amyloid light chain amyloidosis, non-secretory myeloma and combinations thereof.

In some embodiments, the sample is a serum sample, a urine sample, a cerebrospinal fluid sample, or a whole blood sample.

In some embodiments, after diagnosing the subject as having a disorder, the method further includes administering to the subject a therapeutic agent to treat the disorder (e.g., a therapeutically effective amount). The therapeutic agent can include one or more of chlorambucil, fludarabine, cyclophosphamide, bendamustine, carfilzomib, cyclophosphamide, doxorubicin, vincristine, prednisone, chlorambucil, pentostatin, fludarabine, bortezomib, thalidomide, dexamethasone, doxorubicin, ibrutinib, melphalan, adriamycin, lenalidomide, pomalidomide, a bisphosphonate, a glycosaminoglycans, a purine nucleoside analog, and a monoclonal antibody (e.g., rituximab, obinutuzumab, and alemtuzumab).

In some embodiments, the disorder is monoclonal gammopathy of undetermined significance and the therapeutic agent is a bisphosphonates. Non-limiting examples of bisphosphonates include alendronate (e.g., BINOSTO®, FOSAMAX®, risedronate (e.g., ACTONEL®, ATELVIA®), ibandronate (e.g., BONIVA®) and zoledronic acid (e.g., RECLAST®, ZOMETA®)

In some embodiments, the disorder is B-cell chronic lymphocytic leukemia and the therapeutic agent is selected from chlorambucil, fludarabine (e.g., FLUDARA®), cyclophosphamide (e.g., CYTOXAN®), bendamustine, cyclophosphamide, doxorubicin, vincristine (e.g., ONCOVIN®), prednisonea, chlorambucil, obinutuzumab, ofatumumab, pentostatin (e.g., NIPENT®), alemtuzumab (e.g., CAMPATH®), fludarabine, a monoclonal antibody (e.g., rituximab), and combinations thereof.

In some embodiments, the disorder is Waldenstroms macrogloblinemia and the therapeutic agent is selected from bortezomib, thalidomide, fludarabine, dexamethasone, chlorambucil, cyclophosphamide, doxorubicin, vincristine, prednisone, a monoclonal antibody (e.g., rituximab), a purine nucleoside analog (e.g., cladribine), ibrutinib, and combinations thereof.

In some embodiments, the disorder is amyloid light chain amyloidosis and the therapeutic agent is selected from a melphalan, prednisone, vincristine, adriamycin, dexamethasone, bendamustine, thalidomide, cyclophosphamide, lenalidomide, pomalidomide, bortezomib, a glycosaminoglycans (e.g., eprodisate), and combinations thereof.

In some embodiments, the disorder is non-secretory myeloma and the therapeutic agent is selected from thalidomide, bortezomib, lenalidomide, carfilzomib, pomalidomide and combinations thereof.

In some embodiments, after diagnosing the subject as having a disorder, the method further includes performing a treatment such as a plasma exchange or a stem cell transplant (e.g., an autologous peripheral blood stem cell transplantation).

In some embodiments, after diagnosing the subject as having a disorder, the method further includes administering to the subject a therapeutically effective amount of a therapeutic agent to treat the disorder and one or more of a plasma exchange and a stem cell transplant Also, provided herein is a method for diagnosing a monoclonal gammopathy in a subject. The method includes: (a) providing a sample from the subject; (b) subjecting the sample to a mass spectrometry technique to obtain a mass spectrum of the sample; and (c) diagnosing a monoclonal gammopathy in the subject based on the identification of one or more free kappa immunoglobulin light chains or one or more free lambda immunoglobulin light chains.

In some embodiments, the method further includes contacting the sample comprising an immunoglobulin free light chain with a reducing agent prior to subjecting the sample to the mass spectrometry technique.

Additionally, provided herein is a method for monitoring a treatment of a monoclonal gammopathy in a subject. The method includes: (a) providing a first sample of the subject, obtained before the treatment; (b) providing a second sample of the subject obtained during or after the treatment; (c) subjecting the first and second samples to a mass spectrometry technique to obtain a mass spectrum of the first and second samples; (d) determining the concentration of at least one of free kappa immunoglobulin light chain or at least one free lambda immunoglobulin light chain in the first and second samples; and (e) comparing the concentration of the at least one free kappa immunoglobulin light chain or the at least one free lambda immunoglobulin light chain in the first and second samples. The first sample obtained before treatment can be obtained before the start of any treatment, before the start of a particular administration regime, or before a single administration. During the monitoring of treatment, a decrease in the peak height or peak area of an identified immunoglobulin free light chain can indicate that the treatment is progressing positively. Likewise, during the monitoring of treatment, a decrease in concentration of an identified immunoglobulin free light chain can indicate that the treatment is progressing positively. During the monitoring of treatment, an increase in the peak height or peak area of an identified immunoglobulin free light chain can indicate that the dosage of therapeutic agent should be increased. Likewise, during the monitoring of treatment, an increase in concentration of an identified immunoglobulin free light chain can indicate that the dosage of therapeutic agent should be increased.

In some embodiments, the method further includes contacting the first and second samples comprising an immunoglobulin free light chain with a reducing agent prior to subjecting the first and second samples to the mass spectrometry technique.

EXAMPLES

Example 1. Detecting Kappa FLC in a Spiked Sample

Two spiked samples were made using normal pooled serum. Sample A was spiked with 0.5 g/dL HUMIRA® (a monoclonal IgG kappa therapeutic antibody) while sample B was spiked with both HUMIRA® and commercially available kappa light chains at 0.125 g/dL. Next, 50 of each spiked serum was diluted to with 450 µL of MELON™ Gel buffer and added to a spin column and mixed for 5 minutes.

After centrifuging, a 2 µL injection of the purified samples was made onto a 1.0×75 mm Poroshell 300SB-C3, 5 µm column flowing at 25 µL/minute. A 15 minute gradient was started at 80% A/20% B, held for 0.5 minutes, ramped to 70% A/30% B over 1 minute, then ramped to 60% A/40% B over 4 minutes, then ramped to 5% A/95% B over 5 minutes, held for 2.5 minutes, then ramped to 80% A/20% over 1 minute, then equilibrating at 80% A/20% for 1 minute.

Spectra were collected on an ABSciex TripleTOF 5600 quadrupole time-of-flight mass spectrometer (ABSciex, Vaughan ON, CA) in ESI positive mode with a Turbo V dual ion source with an automated calibrant delivery system (CDS). Source conditions were: IS: 5500, Temp: 500, CUR: 45, GS1: 35, GS2: 30, CE: 50±5. TOF MS scans were acquired from m/z 600-2500 with an acquisition time of 100 ms. Fragment ion scans were acquired from m/z 350-2000 with an acquisition time of 100 ms. The instrument was calibrated every 5 injections through the CDS using calibration solution supplied by the manufacturer.

Figure 2B:
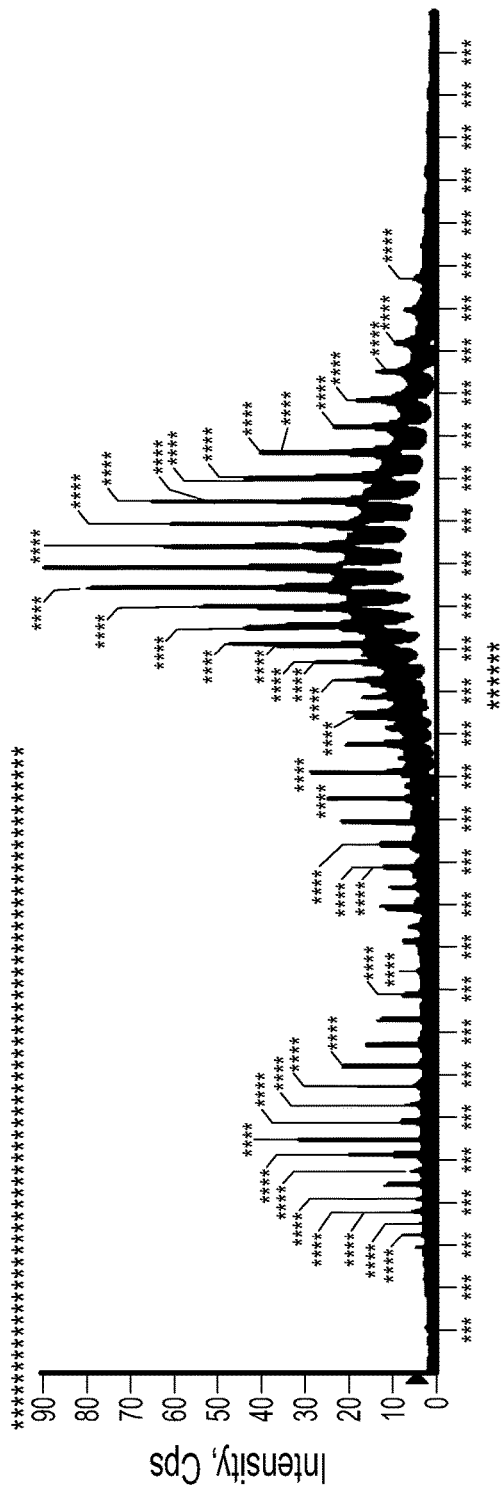
FIG. 2B shows the summed spectra for the LC-MS/MS spectra of normal serum spiked with both kappa free light chains and HUMIRA®

The resulting mass distribution demonstrates the ability to this method detect kappa free light chains (FLCs) from intact monoclonal Igs (HUMIRA®) which is not dependent on the ratio of kappa/lambda FLCs. FIG. 1 shows the results (non-deconvoluted and deconvoluted) of the normal serum spike with HUMIRA® only and demonstrates the detection of the intact Ig. FIG. 2 shows the results of the normal serum spiked with both kappa FLCs and HUMIRA® and demonstrates the methods ability to detect the FLC in the presence of the Intact Ig.

Example 2. Detecting Kappa FLC in a Spiked Sample

Two spiked samples were made using normal pooled serum. Sample A was spiked with 0.5 g/dL HUMIRA® (a monoclonal IgG kappa therapeutic antibody) while sample B was spiked with both HUMIRA® and commercially available lambda light chains at 0.125 g/dL. The samples were subjected to the analysis procedure as described in Example 1.

Figures 4A, 4B:
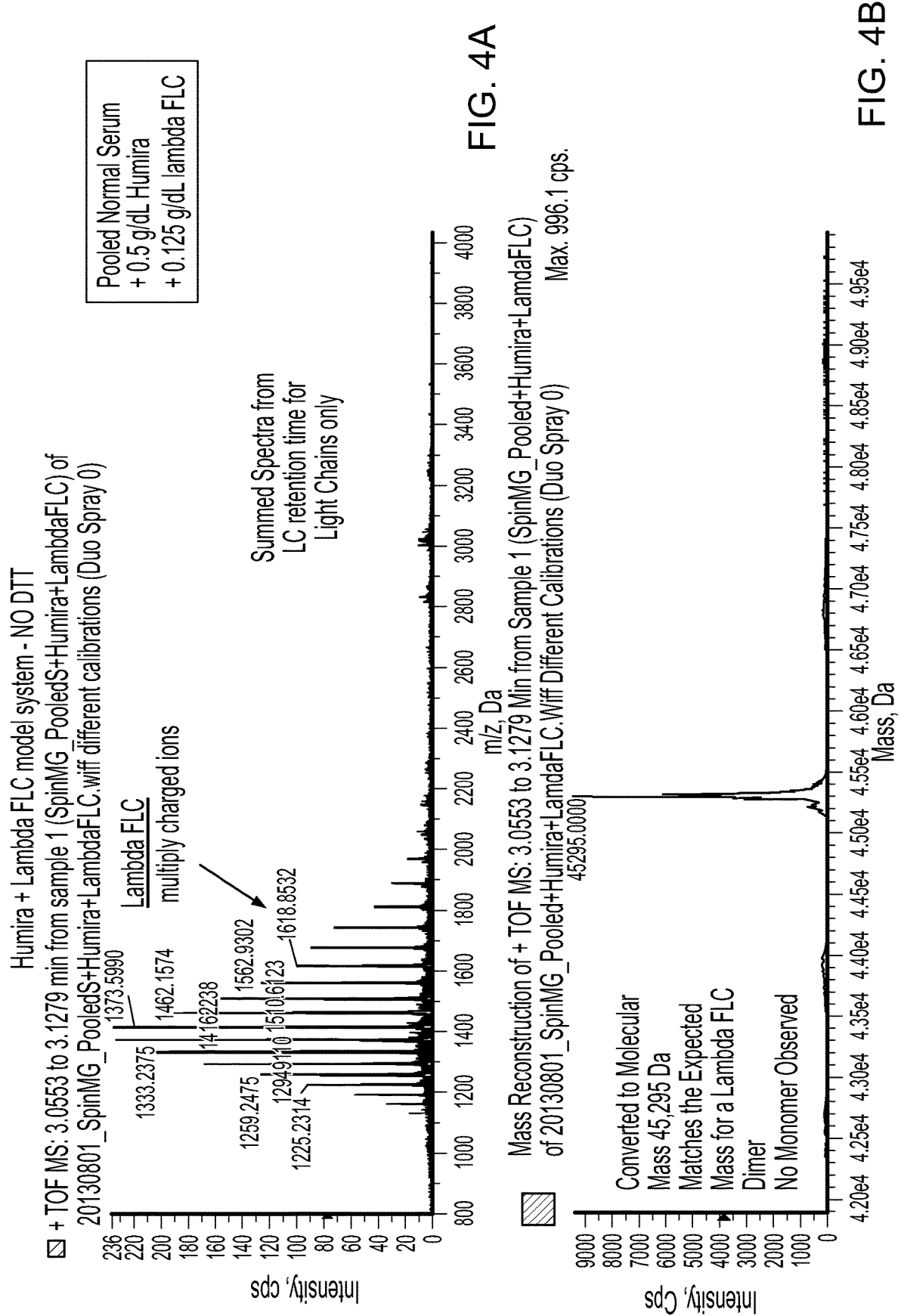
FIG. 4A shows the summed spectra for normal serum spiked with both lambda free light chains and HUMIRA®.
FIG. 4B shows the spectra for normal serum spiked with both lambda free light chains and HUMIRA®, which has been deconvoluted to show molecular mass.

The resulting mass distribution demonstrates the ability to this method detect lambda free light chains (FLCs) from intact monoclonal Igs (HUMIRA®), which is not dependent on the ratio of kappa/lambda FLCs. FIG. 3 shows the results of the normal serum spiked with both lambda FLCs and HUMIRA® and demonstrates the ability to detect FLC in the presence of intact Ig. In this example, as shown in FIG. 4, the method was able to confirm not only the presence of the FLC but also demonstrate that the light chain was circulating as a dimer.

Example 3. Measuring FLC Quantities in Serum

Figure 5:
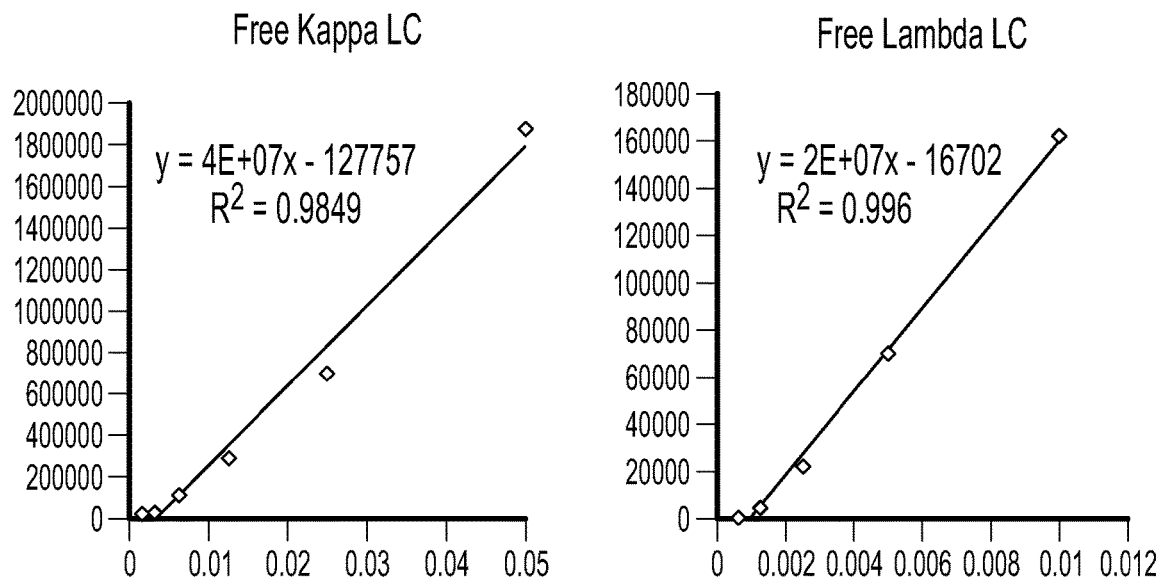
FIG. 5. Shows the LC-MS/MS results for serial dilutions of kappa immunoglobulin free light chains and lambda free light chains.

Serial dilutions of the kappa and lambda FLCs were made by diluting normal human serum spike with kappa and lambda free light chains. Quantitation of the amount of free light chain was performed using the procedure described in Example. FIG. 5 shows that the peak area of the FLC is directly proportional to the concentration of FLC in serum.

Example 4. Precision of FLC Measurement

Human serum was spiked with 0.125 g/dL kappa FLC and was repeatedly measured 12 times using the procedure described in Example 1. The peak area percent variation was determined to be 8.8%. This amount of variation is acceptable for clinical practice.

Example 5. Detecting FLC in a Patient with a Monoclonal Gammopathy

Serum from a 77 year old MGUS (monoclonal gammopathy of undetermined significance) patient (A) with an IgG kappa monoclonal gammopathy with an associated abnormal kappa/lambda FLC ratio of 3.81 by nephelometry was examined using the procedure described in Example 1. A second sample from the same patient was treated with DTT (dithiothreitol) reducing agent to separate the light and heavy chains prior to Ig isolation and measurement.

Figure 6A:
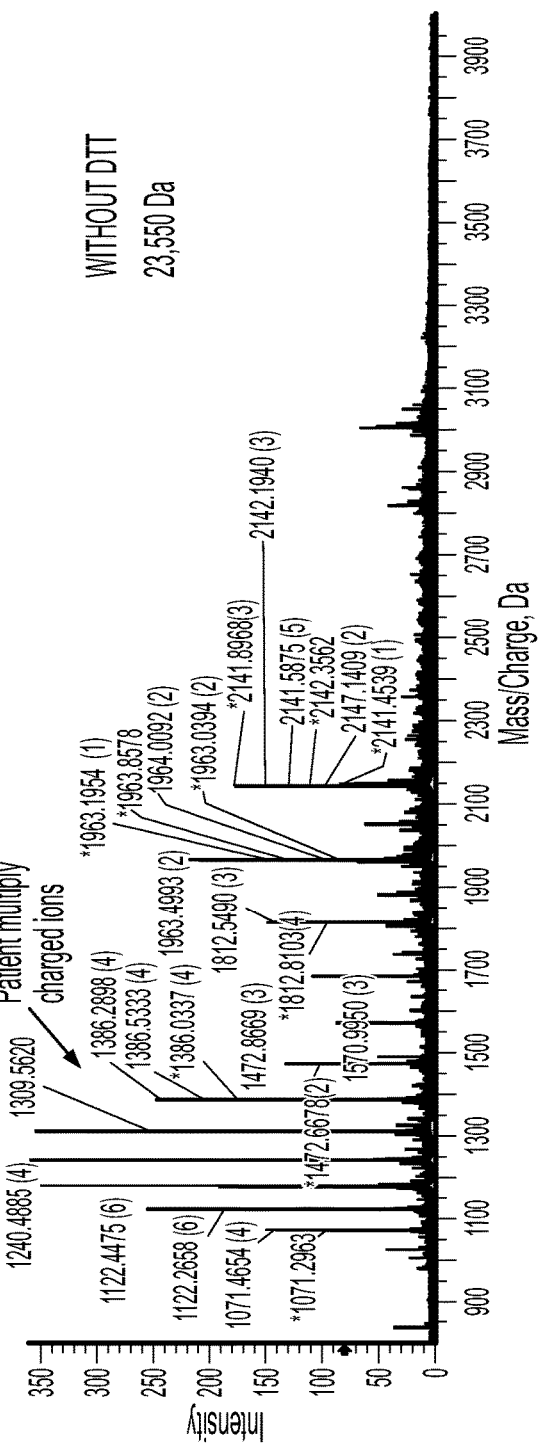
FIG. 6. Shows the LC-MS/MS spectra for serum—that has been treated (FIG. 6A), or has not been treated, with dithiothreitol (FIG. 6B)—taken from a patient diagnosed with a monoclonal gammopathy of undetermined significance.
Figure 6B:
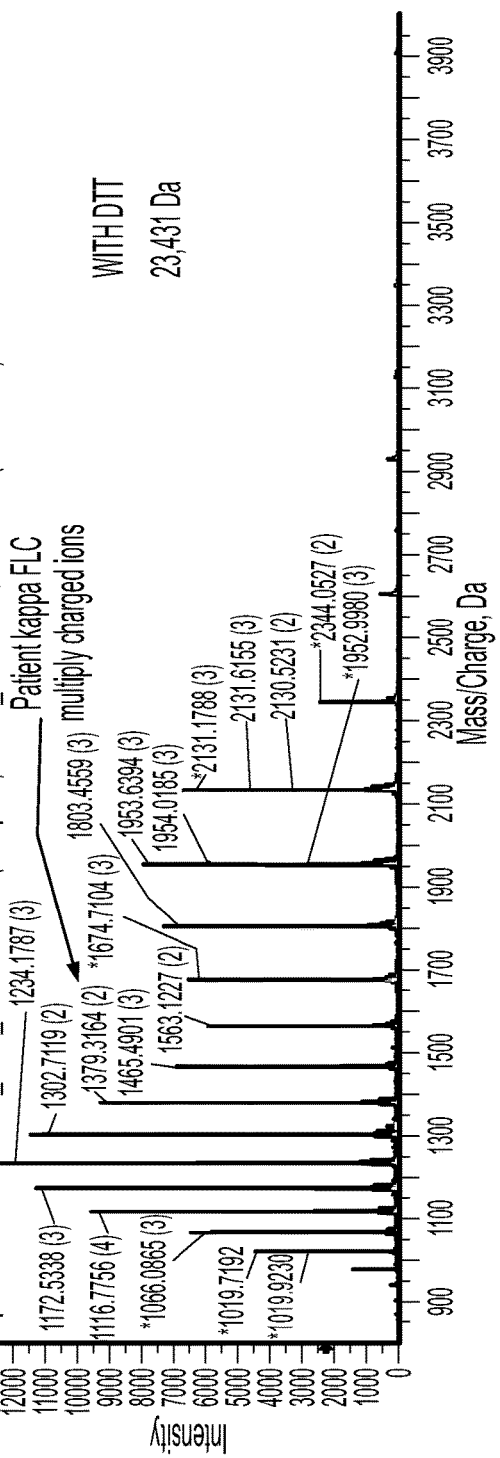

The resulting spectra are shown in FIGS. 6A and 6B and demonstrate that kappa FLC has a slightly different mass than the kappa clone associated with the intact IgG kappa. FIG. 7 shows that by using top-down mass spectrometry, the fragmentation pattern reveals a kappa constant region for each ion.

Example 6

Figure 8A:
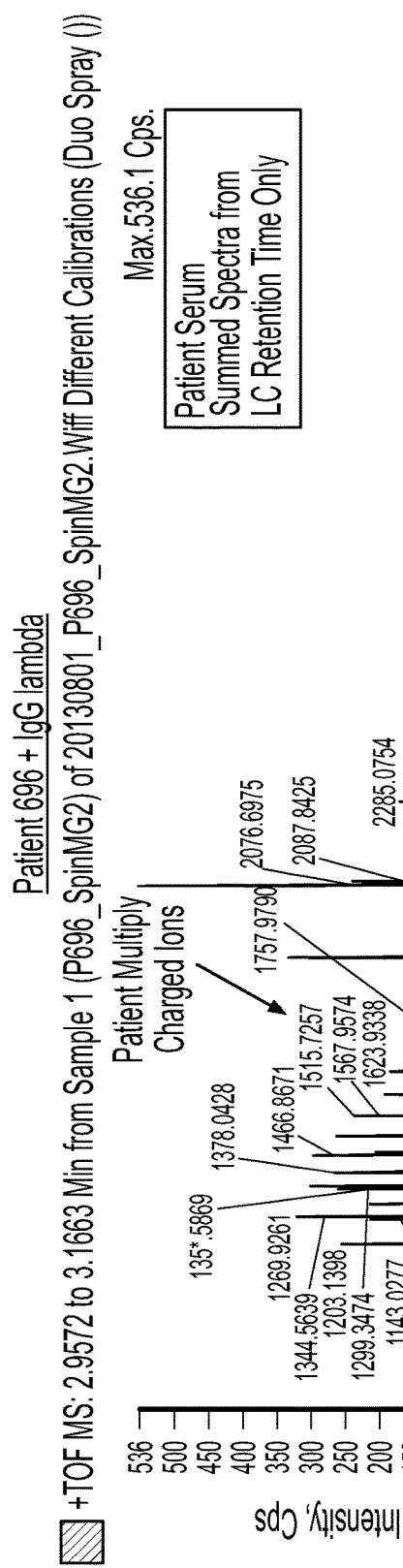
FIG. 8A shows the summed mass spectra for serum taken from a patient diagnosed with smoldering myeloma.
Figure 8B:
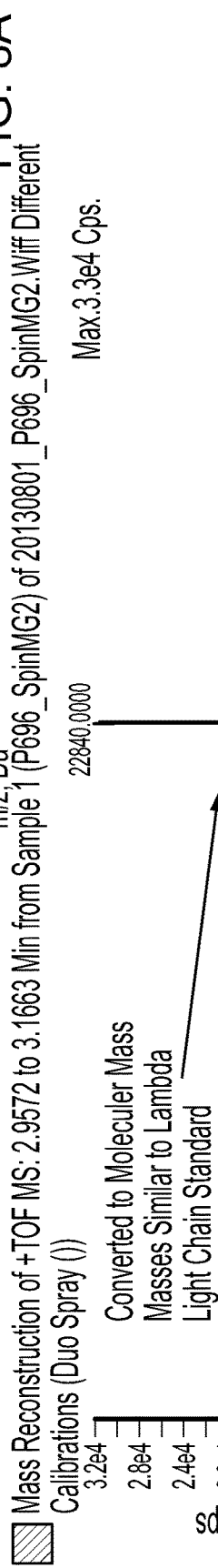
FIG. 8B shows the spectra for serum taken from a patient diagnosed with smoldering myeloma, which has been deconvoluted to show molecular mass.

Serum from a 70 year old smoldering myeloma patient (A) with an IgG lambda monoclonal gammopathy with an associated abnormal kappa/lambda FLC ratio of 0.483 by nephelometry was examined using the procedure described in Example 1. The resulting spectra are shown in FIG. 8 and demonstrate the presence of multiple lambda based clones. The ability to detect multiple FLC is unique to this method.

Example 7

Materials
Serum Samples:
Fifteen serum samples from patients with AL were obtained under patient informed consent associated with the amyloid biobank IRB protocol 521-93 at the Mayo Clinic in Rochester Minn. An additional fifteen serum samples from patients with AL were obtained under patient informed consent associated with the amyloid biobank (Giampaolo please fill in the IRB number) at IRCCS Policlinico San Matteo in Pavia, Italy.

Reagents:
Ammonium bicarbonate, dithiothreitol (DTT), and formic acid were purchased from Sigma-Aldrich (St. Louis, Mo.). Water, acetonitrile, and 2-propanol were purchased from Honeywell Burdick and Jackson (Muskegon, Mich.).

Monoclonal Immunoglobulins:
The therapeutic monoclonal immunoglobulin adalimumab (Humira) was purchased from Abbott Laboratories (Chicago, Ill.). Lambda and Kappa immunoglobulin light chain standards were purchased from Bethyl Laboratories (Montgomery, Tex.). The standards were purified from the urine of patients with multiple myeloma who consented to have their urine used as a source for a monoclonal immunoglobulin light chain standard. The concentration of each standard was confirmed using The Binding Site FLC nephelometric assay. Bradwell A R, Carr-Smith H D, Mead G P, et al. "Highly sensitive, automated immunoassay for immunoglobulin free light chains in serum and urine." *Clinical chemistry.* 2001; 47(4):673-680.

Serum FLC Preparation:
A volume of 20 µL of serum was mixed with 200 µL of MELON™ GEL bead slurry in a 1.5 mL microcentrifuge tube (Thermo-Fisher Scientific, Waltham Mass.). The serum and beads were mixed on a shaker for 5 minutes at room temperature after which the beads were allowed to settle. A volume of 20 µL of MELON™ GEL supernatant containing the FLC was removed and mixed with 20 µL of 50 mM ammonium bicarbonate and then analyzed by microLC-ESI-Q-TOF MS MELON™ GEL purified samples were also analyzed after reduction with DTT. In this case a volume of 20 µL of MELON™ GEL supernatant was mixed with 20 µL of 50 mM ammonium bicarbonate 10 µL of 200 mM DTT and allowed to reduce at 55° C. for 15 minutes before being analyzed by microLC-ESI-Q-TOF MS.

LC Conditions:
An Eksigent Ekspert 200 microLC (Dublin, Calif.) was used for separation; mobile phase A was water+0.1% FA, and mobile phase B was 90% acetonitrile+10% 2-propanol+0.1% FA. A 2 µL injection was made onto a 1.0×75 mm Poroshell 300SB-C3, 5 µm column heated to 60 and flowing at 25 µL/minute. A 25 minute gradient was started at 80% A/20% B, held for 1 minute, ramped to 75% A/25% B over 1 minutes, then ramped to 65% A/35% B over 10 minutes, then ramped to 50% A/50% B over 4 minutes, then ramped to 95% A/5% B over 2 minutes held for 5 minutes, then ramped to 80% A/20% over 1 minute, then equilibrating at 80% A/20% for 1 minute.

ESI-Q-TOF MS:
Spectra were collected on an ABSciex TripleTOF 5600 quadrupole time-of-flight mass spectrometer (ABSciex, Vaughan ON, CA) in ESI positive mode with a Turbo V dual ion source with an automated calibrant delivery system. Source conditions were: IS: 5500, Temp: 500, CUR: 45, GS1: 35, GS2: 30, CE: 50±5. TOF MS scans were acquired from m/z 600-2500 with an acquisition time of 100 ms. The instrument was calibrated every 5 injections through the CDS using calibration solution supplied by the manufacturer.

MS Data Analysis:
Analyst TF v1.6 was used for instrument control. Data were viewed using Analyst TF v1.6 and PeakView v1.2.0.3.

Multiply charged ion peak centroids were used to calculate average molecular mass and the peak area value used for quantification through BioAnalyst software provided with Analyst TF. Multiple ion deconvolution was performed using the Bayesian Protein Reconstruct software package in BioAnalyst. The following settings were used: Start mass (Da)=22,000, Stop mass (Da)=65,000 Da, Step mass (Da) =1, S/N threshold=20, Minimum intensity %=0, Iterations=20, Adduct: Hydrogen. All masses are reported as average molecular mass.

Results.

Purified FLC and Adalimumab in Normal Serum as a Model System

Figure 9:
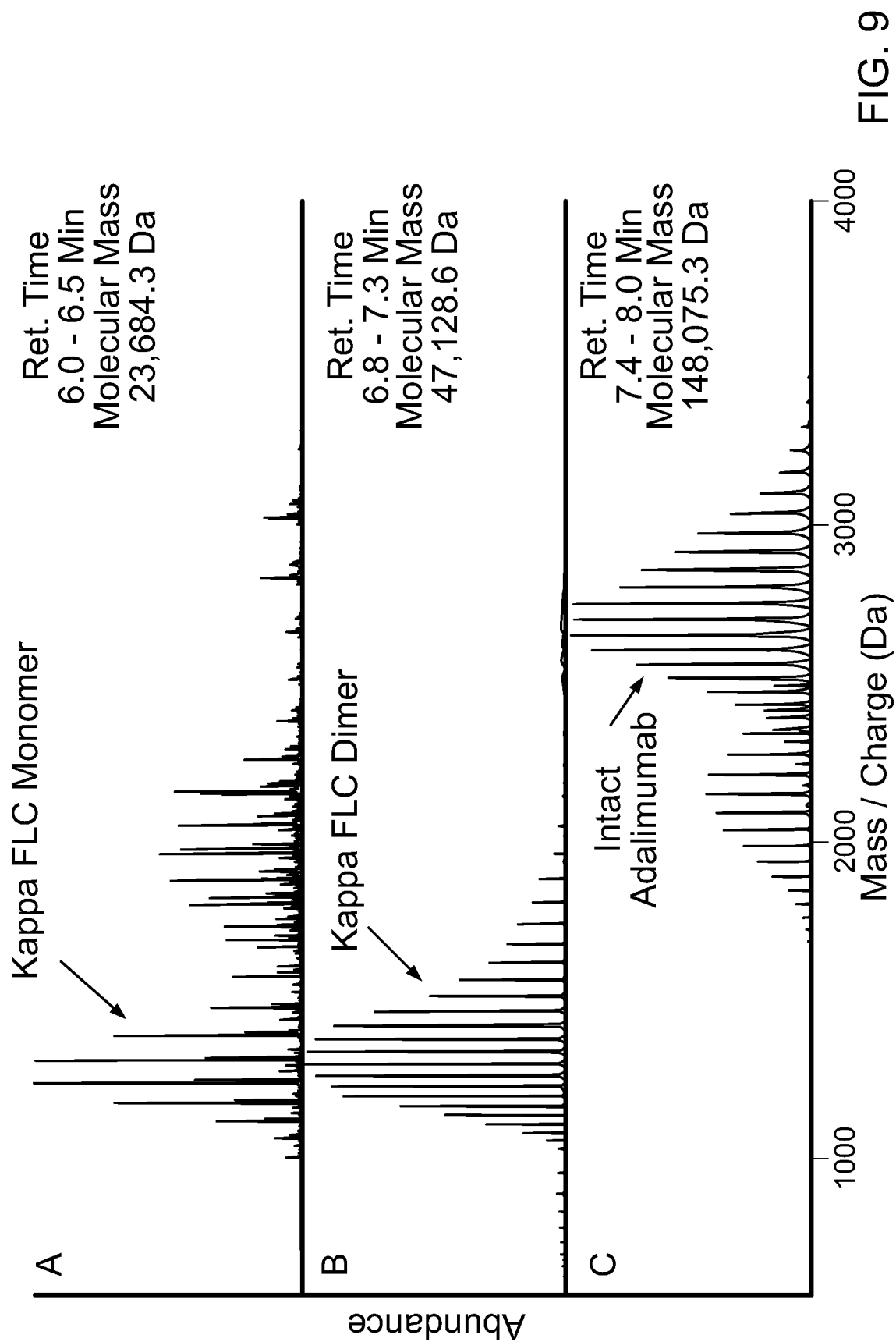
FIG. 9. Shows a mass spectra from pooled serum spiked with both adalimumab (500 mg/L) and purified kappa FLC (100 mg/L). The spectra are as follows: (i)

It has previously been shown that the therapeutic mAb adalimumab works well as a standard for simulating a monoclonal immunoglobulin in serum. In the set of experiments presented here, adalimumab and purified kappa FLC was spiked into serum pooled from healthy individuals. FIG. 9 shows three mass spectra acquired from pooled serum spiked with both adalimumab at a concentration of 500 mg/L and purified kappa FLC at a concentration of 100 mg/L. The mass spectrum labeled A was generated by summing mass spectra over a retention time of 6.0 to 6.5 minutes and clearly shows the multiple charge states for the monomer form of the kappa FLC between m/z=1,000 to 1,500 Da. There is also a heterogeneous set of other multiply charged ions observed above m/z=1,500. The most abundant ions are associated with a protein having a molecular mass of 45,056.5 Da, which is likely the most common glycoform of alpha-1-antitrypsin (A1AT). These peaks are also found in normal pooled serum. The mass spectrum labeled B was generated by summing mass spectra over a retention time of 6.8 to 7.3 minutes and clearly shows the dimer form of the kappa FLC between m/z=1,000 to 1,500 Da. The mass spectrum labeled C shows the intact adalimumab at a retention time of 7.4 to 8.0 minutes where the multiply charged ions from the mAb are found between m/z=2,500 to 3,500 Da. The other multiply charged ions observed between m/z=1,800 to 2,200 have a calculated molecular mass of 79,551.9 Da and is likely transferrin (Tf) which is present in normal pooled serum without kappa FLC. It is known that MELON™ GEL does not completely deplete transferrin from serum. Imprecision in the microLC-ESI-Q-TOF MS portion of the methodology was examined by performing 20 replicate injections from the same well of 100 mg/L kappa FLC spiked into normal pooled serum. The peak area from the extracted ion chromatogram (EIC) generated using the +18 charge state for the monomer (FIG. 9A, m/z=1,316.78 Da) and the +36 charge state for the dimer (FIG. 9B, m/z=1,310.11 Da) were used to calculate the % CV values. The % CV's were; 5.6 for the monomer, 3.5 for the dimer, and 6.6 for the ratio of dimer to monomer. Serial dilutions (100, 50, 25, 12.5, 6.25. 3.12) were also prepared starting with the 100 mg/L kappa FLC spiked into normal pooled serum diluted with normal serum. Linear regression analysis of the monomer and dimer were performed using the EIC peak areas. The monomer linear regression analysis of the serial dilutions had an $R^2$=0.996 while the dimer linear regression analysis had an $R^2$=0.993. The monomer was detected from 6.25 mg/L to 100 mg/L while the dimer was detected from 3.12 mg/L to 100 mg/L. The molecular masses for the kappa FLC monomer and dimer and the adalimumab are also listed in FIG. 9. The calculated molecular mass of the monomer found by dividing the dimer by two and adding the mass of a proton is 23,565.3 Da. The difference in the mass between the observed monomer mass and the calculated monomer mass (23,684.3-23,565.3) equals 119.0 Da. This mass matches the molecular mass of a cysteinylated cysteine residue. After adding DTT to the sample the dimer was no longer observed and the molecular mass of the monomer was 23,565.3 Da. Imprecision was also examined on 20 replicate injections from the same well of a 100 mg/L purified lambda FLC spiked into normal pooled serum. In these spectra only the dimer of the lambda FLC was observed. To generate the EIC the +33 charge state of the dimer (m/z=1,373.56 Da) was used and a % CV of 6.9 was found for the peak areas from the replicate injections.

AL Patient Cohort Comparison

After demonstrating that FLC could be enriched from serum using MELON™ GEL, a cohort of 30 patients with confirmed cases of amyloidosis (15 from the Pavia biobank and 15 from the Mayo biobank) was examined. All patient samples were examined in their non-reduced (no DTT; FLC present) and reduced (with DTT; all light chains observed) forms using the same methodology as described for the model FLC preparations. The process of determining the FLC and non-FLC light chains in patient samples is presented in below for an AL patient with a known lambda FLC.

Figure 10:
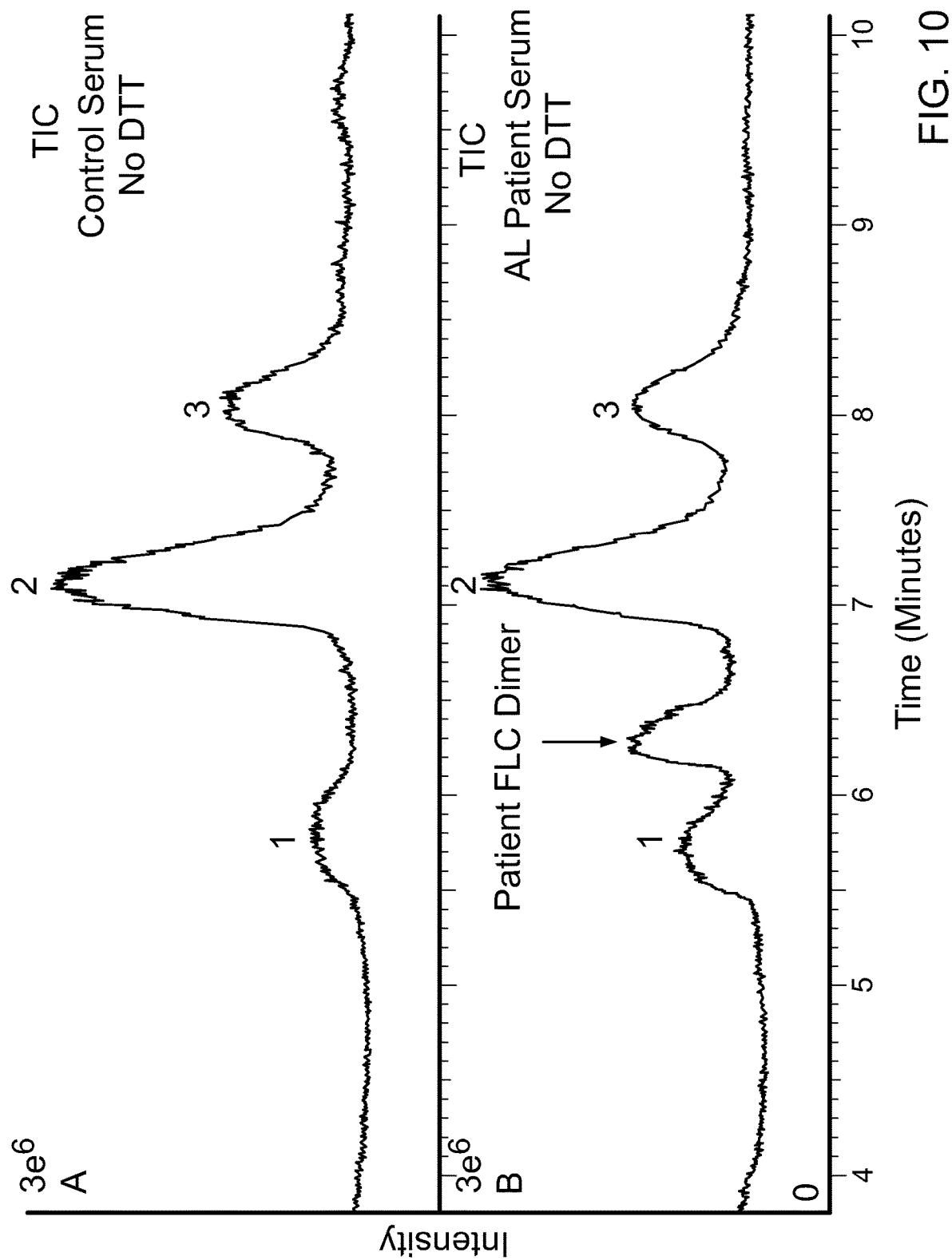
FIG. 10. Shows a total ion chromatograms (TIC) from serum after enrichment using MELON™ GEL.
Figure 11:
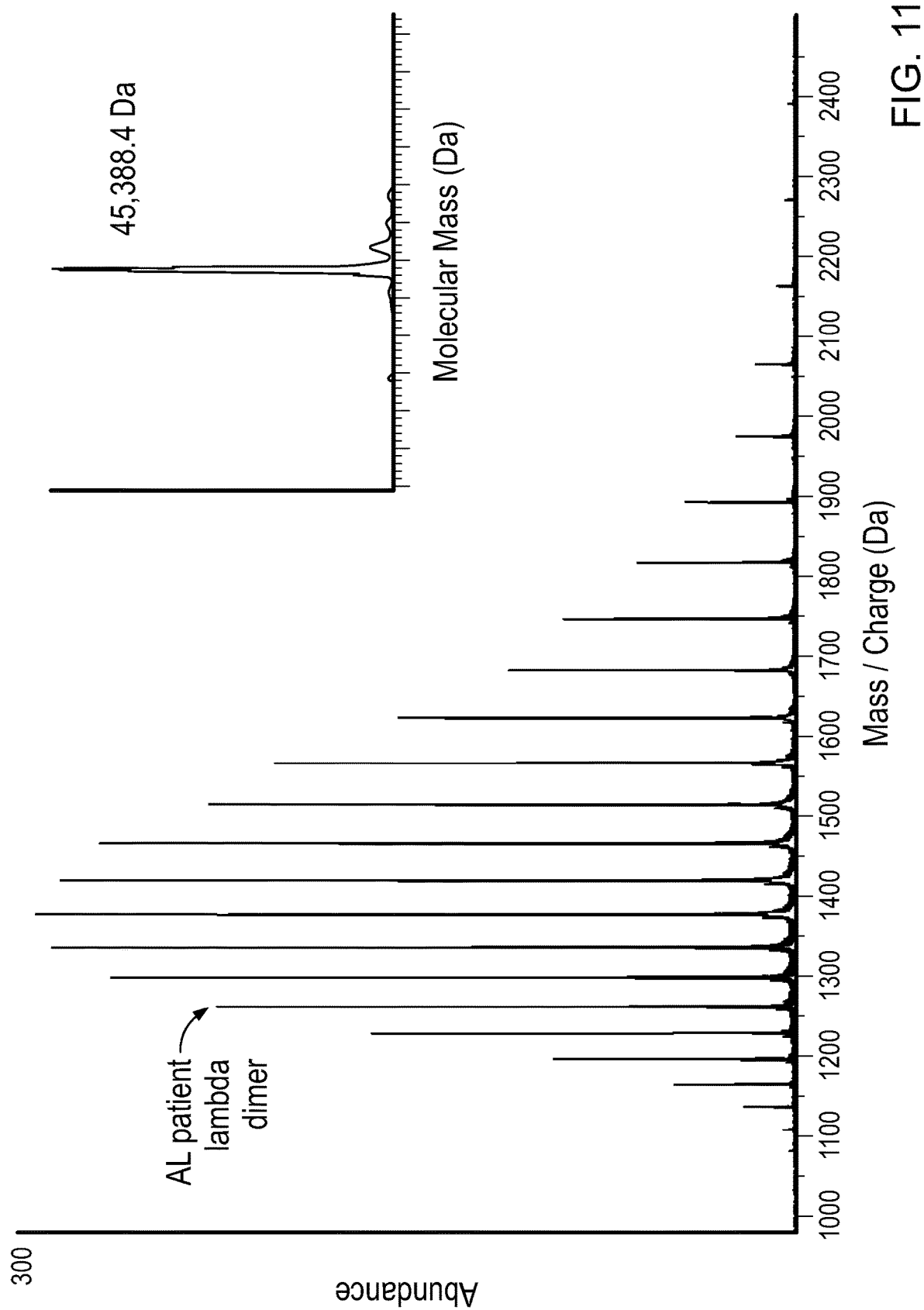
FIG. 11. Shows a mass spectrum observed after summing spectra over the retention time of the FLC dimer peak shown in FIG. 10. The multiply charged ions were deconvoluted to determine the molecular mass of the dimer shown in the inset.
Figure 12:
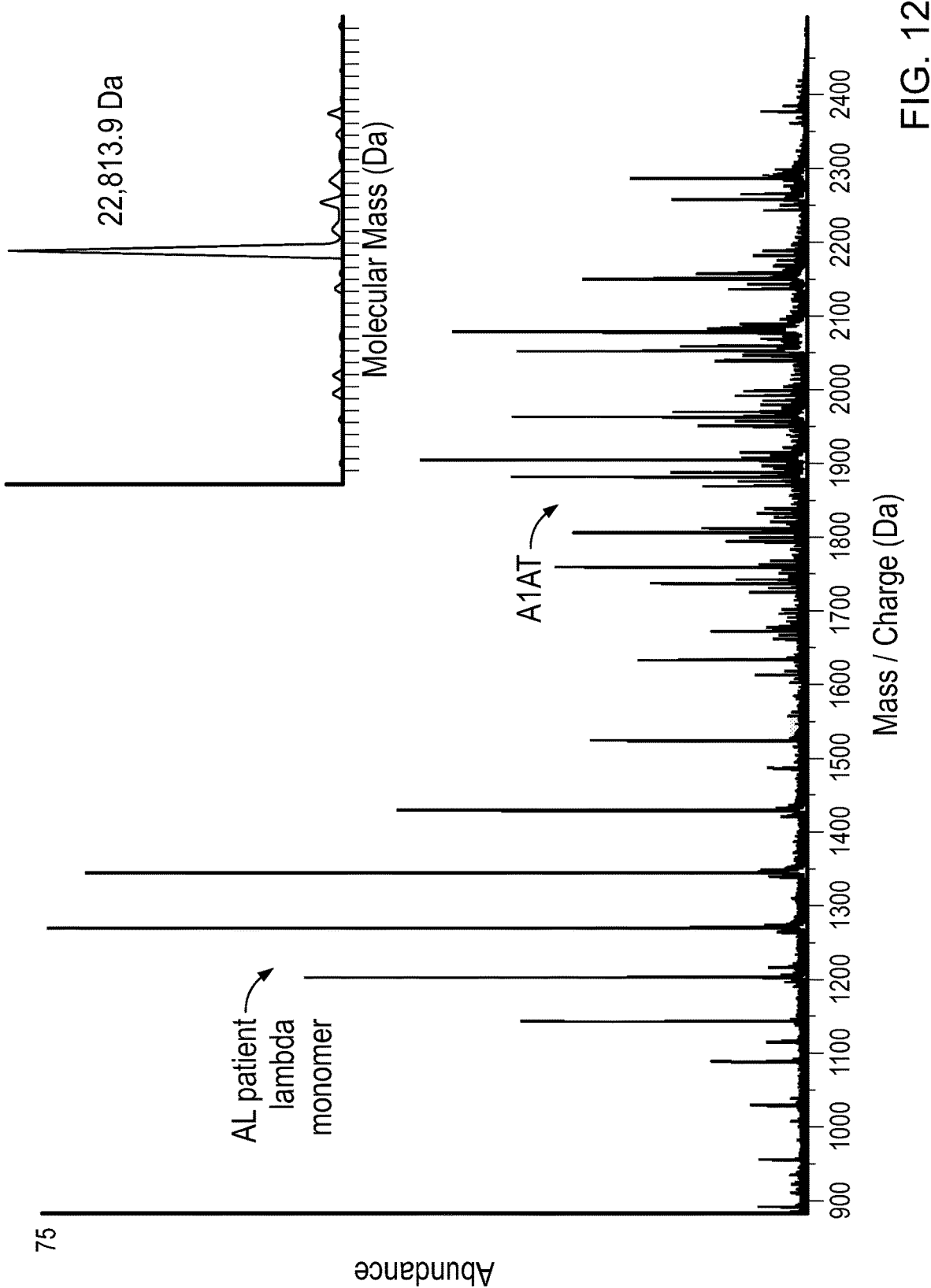
FIG. 12. Shows a mass spectrum showing the FLC monomer along with the inset that shows the molecular mass found after deconvolution of the mass spectrum. The spectrum also shows the multiply charged ions from A1AT which co-elutes with the lambda monomer.

An example of a total ion chromatogram (TIC) from non-reduced serum is shown in FIG. 10 where the normal serum TIC is labeled A and the patient with AL serum TIC is labeled B. The TICs have three peaks labeled 1, 2, and 3 presumed to be alpha-1-antitrypsin (A1AT), transferrin (Trf), and an unknown 61 kDa protein, respectively. However, the TIC from the AL patient shows a peak that is not observed in the control at a retention time of 6.3 minutes. FIG. 11 shows the mass spectrum observed after summing mass spectra over the retention time of this peak. The mass spectrum clearly shows a series of multiply charged ions and the inset shows the deconvoluted spectrum for these ions with the calculated molecular mass of 45,388.4 Da. These ions were assumed to be a dimer comprised of two FLC lambda monomers each with a monomer molecular mass of 22,699.2 Da (45,388.4/2+1H (reduced cysteine that formed the dimer)+4H (reduced internal disulfide bonds). The monomer form of the FLC was not readily apparent by observing the TIC alone. To identify the monomer, mass spectra were summed over 30 second retention time windows and manually searched. The FLC monomer was found to coelute with peak 1 with a retention time of 5.5 to 6.6 minutes. The isotype of the FLC was confirmed to be lambda using top-down MS. FIG. 12 shows the mass spectrum generated over this retention time which shows that the peak contains two different sets of multiply charged ions. Deconvolution of the ions within the range m/z=1,000 to 1,600 resulted in a single peak with a molecular mass of 22,813.9 Da as shown in the inset to FIG. 12. Deconvolution of the ions within the range m/z=1,700 to 2,400 resulted in multiple ions that matched the A1AT isoforms observed in the normal control serum.

Figure 13:
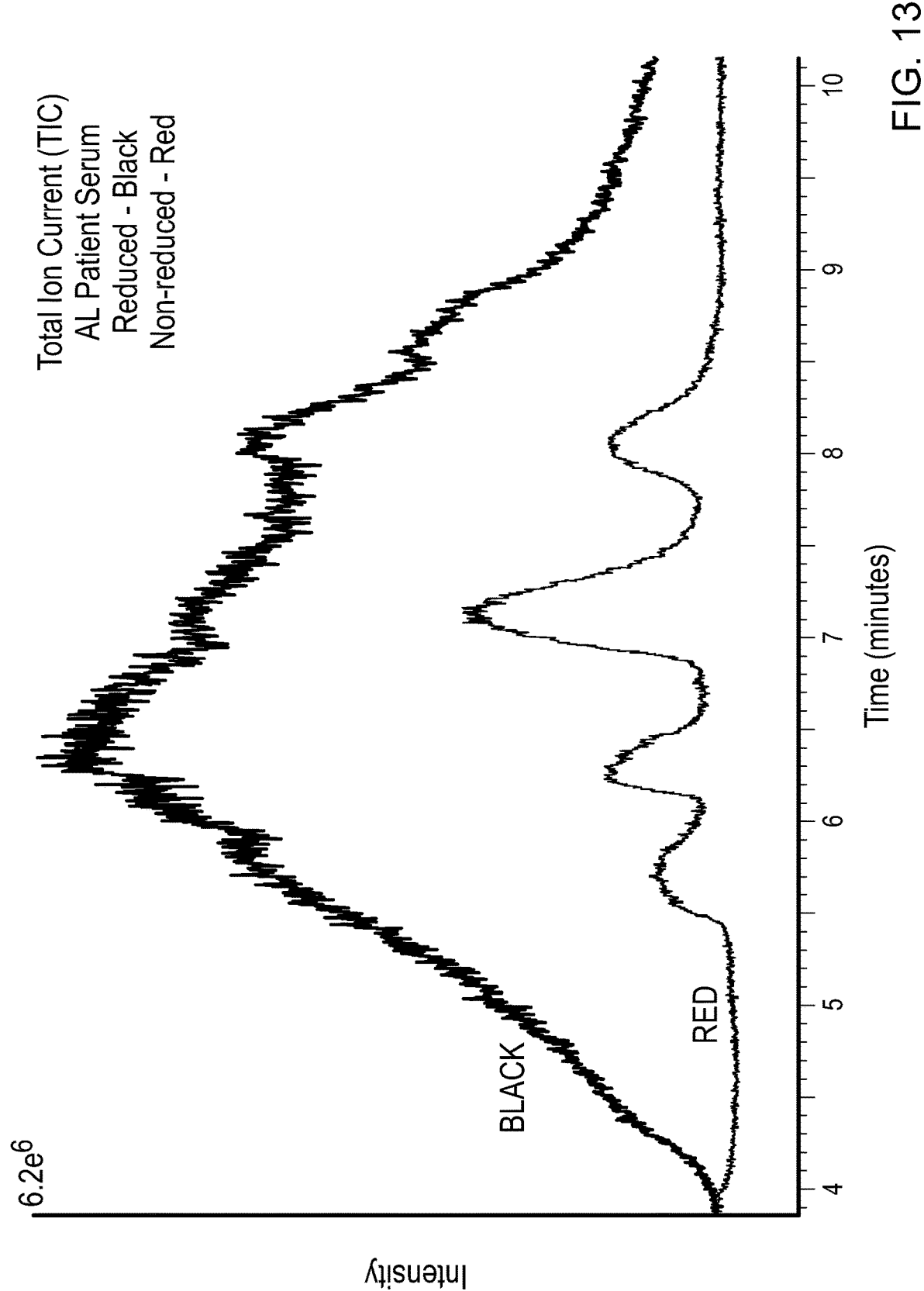
FIG. 13. Shows a total ion chromatograms (TIC) from the same AL patient MELON™ GEL enriched serum sample reduced with DTT (black trace) and non-reduced (no DTT) red trace; same as FIG. 10B. The TIC shows that the response from the monoclonal FLC is not as pronounced in the reduced sample as the non-reduced sample as a result of the substantial increase in the response observed in the mass spectrometer by the polyclonal light chains as they are reduced off of their corresponding heavy chains.
Figure 14:
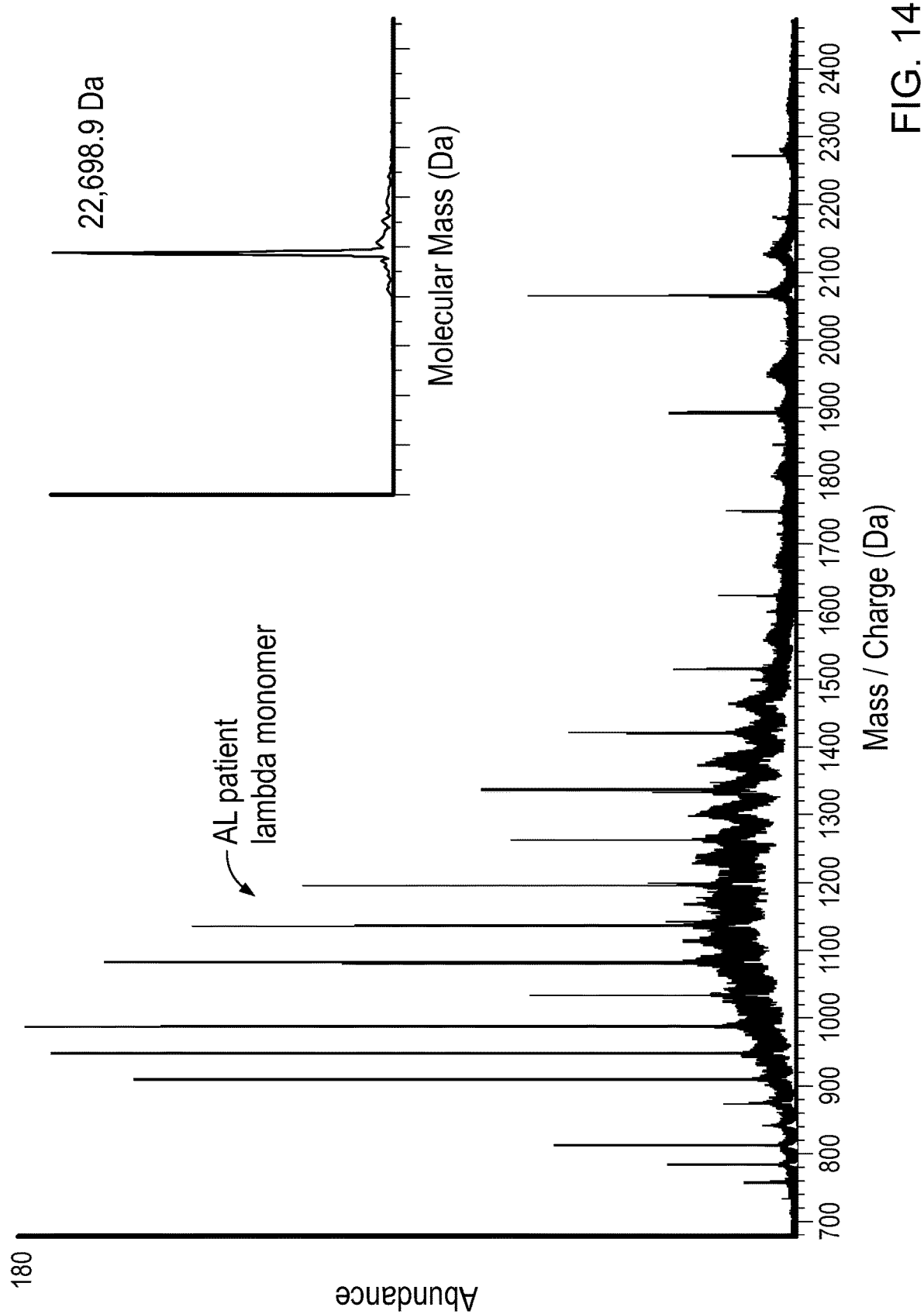
FIG. 14. Shows a mass spectrum showing the FLC lambda monomer multiply charged ions from the AL patient serum in its reduced form. The inset shows the molecular mass of the reduced monoclonal lambda light chain after deconvolution. The mass spectrum also shows at m/z=2100 the polyclonal lambda and kappa+11 charge states with the lambda monoclonal light chain clearly observed in the lambda polyclonal distribution.

Since the calculated molecular mass of the monomer did not match the observed mass of the monomer, the sample was reduced with DTT. The goal of this experiment was to; 1) determine if the dimer would be reduced into two monomers; and 2) determine if the molecular mass of the resulting monomer matched the molecular mass of the FLC monomer. FIG. 13 shows an overlay of the TIC's from the same sample before (red trace) and after (black trace) the addition of DTT. The intensity of the TIC from the reduced sample in FIG. 13 is over two-fold higher than the TIC shown in FIG. 10 from the non-reduced samples. This is due to the contribution to the overall ion current from the polyclonal kappa and lambda light chains and their corresponding heavy chains that are now observed by the mass spectrometer since they are in their reduced form where the multiply charged ions from these species are now within the m/z scan range window of the experiment. An FLC monomer was observed after manually summing mass spectra in 30 second retention time intervals and was found to have a retention time of 6.2 to 6.7 minutes. The multiply charged ions found in this retention time window are shown in FIG. 14. The calculated of molecular mass of these multiply charged ions was found to be 22,698.9 Da as seen in the inset. The isotype of the monoclonal light chain was confirmed to be lambda by top-down MS 4. There is only a 0.3 Da mass difference from the calculated molecular mass of the lambda light chain monomer and the observed molecular mass from FIG. 14.

Figure 15:
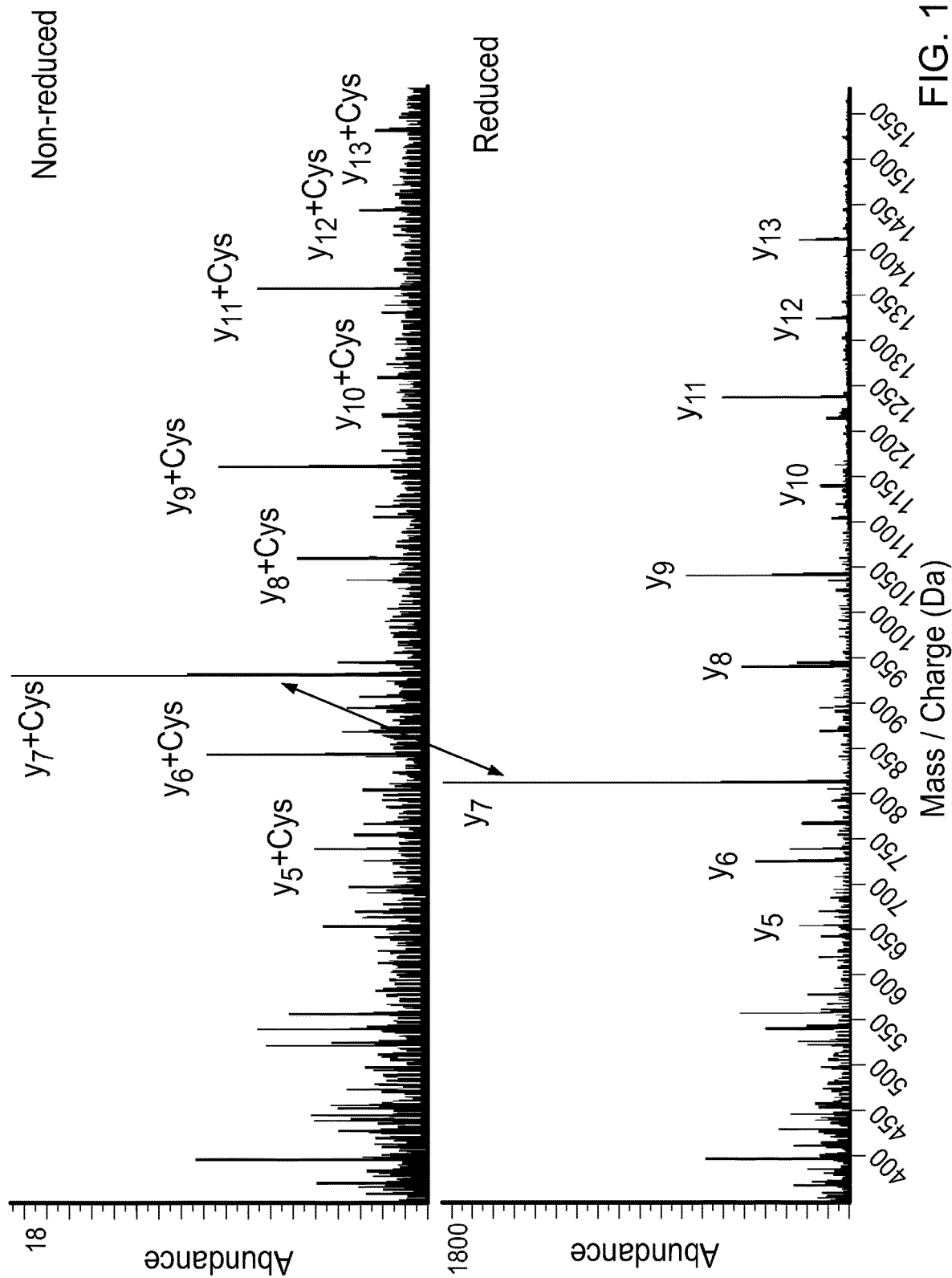
FIG. 15. Shows a top-down MS fragment ion mass spectrum showing the C-terminal y-ions from a cysteinylated kappa FLC in its non-reduced form (top) and non-cysteinylated kappa light chain in reduced form (bottom). The $y_7$+ cysteinylation fragment ion and $y_7$ fragment ion are labeled with an arrow to show the difference in the mass due to cysteinylation of the C-terminal cysteine residue.

The molecular mass of the monomer in the non-reduced sample is 116 Da greater in mass than the monomer observed in the reduced sample, which is close to the known post-translation modification due to cysteinylation (addition of +119 Da) of the C-terminal cysteine as previously described by others. Several of the AL patients in the cohort examined using the methods disclosed herein (e.g., monoclonal immunoglobulin Rapid Accurate Mass Measurement—miRAMM) had kappa FLC. Top-down MS was performed on non-reduced and reduced kappa FLC monomers that displayed a mass difference of +119 Da indicative of cysteinylation. FIG. 15 shows top-down MS mass spectra from a non-reduced (top) and reduced (bottom) kappa FLC monomer. Monoclonal kappa light chains produce predominantly C-terminal y-ions by top-down MS 4 and as a result, each C-terminal fragment ion from the non-reduced FLC is +119 Da greater in mass compared to the reduced FLC since the cysteinylation takes place at the C-terminal cysteine. This observation confirms the position of the cysteinylation in the kappa FLC monomer and is the first report using top-down MS to characterize cysteinylation in a monoclonal light chain.

Results from the AL patient cohort examined using the methods disclosed herein are listed in Table 1. The table lists the non-reduced FLC molecular mass, the occurrence of monomer and/or dimers, observed post-translational modifications (PTM), the reduced FLC molecular mass, and the FLC isotype. The table highlights the extraordinary specificity of the methods disclosed herein for identifying FLC in serum as evident by the accurate molecular mass data. However, the methods disclosed herein also provide information on the presence of dimers and/or monomers and PTM's in the same analysis. For example, the sample Pavia 7 had two monomer and two dimer FLC isoforms along with PTM's cysteinylation and glutathionylation. The glutathionylation was presumed to be present since the mass difference between the two distinct monomers and dimers in the non-reduced sample was 305 Da which is equal to the mass of a glutathione addition to a cysteine residue 21. This mass difference is also observed in the monomers in the reduced sample which suggests that the PTM is stable under the reducing conditions used 22. The cysteinylation PTM was assumed since the observed mass difference between the FLC monomers in the non-reduced sample and the reduced sample is 117 Da, which would equate to the loss of cysteinylation (+119 Da) followed by the loss of 2 hydrogens after interdisulfide bond reformation. Patients that showed a loss in the range of −116 to −119 Da between the non-reduced sample and the reduced sample were labeled as having evidence for cysteinylation. Several of the patients had FLC that exhibited glycosylation as evidenced by the increased molecular mass of the FLC and the oligoclonal nature (2 to 4 glycoforms) of the LC mass speaks that differed by a hexose (162 Da) that were conserved in both the non-reduced and reduced samples and only the most abundant glycoforms are listed in Table 1.

TABLE 1

| Biobank | Non-Reduced Molecular Mass | Non-Reduced FLC isoform | PTM | Reduced Molecular Mass | Isotype |
| --- | --- | --- | --- | --- | --- |
| Pavia 1 | 50,550 | Dimer | glycosylation | 25,280 | L |
| Pavia 2 | 22,815 + 45,388 | Dimer + Monomer | cysteinylation | 22,699 | L |
| Pavia 3 | 23,463 | Monomer | cysteinylation | 23,344 | K |
| Pavia 4 | 26,371 + 52,504 | Dimer + Monomer | glycosylation + cysteinylation | 26,252 | K |
| Pavia 5 | 46,960 | Dimer | | 23,484 | L |
| Pavia 6 | 22,804-22,922 | Monomer | cysteinylation | 22,804 | L |
| Pavia 7 | 22,814 + 23,119/ 45,694 + 45,999 | Dimer + Monomer | cysteinylation + glutathionylation | 22,697 + 23,002 | L |
| Pavia 8 | 22,664 | Monomer | | 22,731 | L |
| Pavia 9 | No FLC's observed | | | 24,264 | K |
| Pavia 10 | 45,480 | Dimer | | 22,745 | L |
| Pavia 11 | 47,140 | Dimer | | 23,572 | K |
| Pavia 12 | 45,290 | Dimer | | 22,584 + oligo | L |
| Pavia 13 | 44,612 | Multiple Dimers | | 22,310 | L |
| Pavia 14 | 23,333 | Monomer | cysteinylation | 23,214 | L |
| Pavia 15 | 45,247 | Dimer | | 22,764 | L |
| Mayo 1 | 23,730 + 47,220 | Dimer + Monomer | | 23,546 | K |
| Mayo 2 | 23,055 + 45,866 | Dimer + Monomer | cysteinylation | 22,937 | L |
| Mayo 3 | 23,486 | Monomer | | 23,331 | K |
| Mayo 4 | 26,126 | Monomer | glycosylation | 23,578 | K |
| Mayo 5 | 45,488 | Monomer | | 22,748 | L |
| Mayo 6 | No FLC's observed | | | 22,655 | L |
| Mayo 7 | 46,059 + 46,221 | Dimer | glycosylation | 23,031 + 23,193 | L |
| Mayo 8 | 23,345 + 46,449 | Dimer + Monomer | cysteinylation | 23,226 | L |
| Mayo 9 | 23,471 + 46,701 | Dimer + Monomer | cysteinylation | 23,355 | K |
| Mayo 10 | 23,589 + 46,938 | Dimer + Monomer | | 23,473 | K |
| Mayo 11 | 45,938 | Dimer | | 22,837 | L |
| Mayo 12 | 47,643 + 47,805 | Dimer | glycosylation | 23,056 + 23,218 | L |

Figure 16:
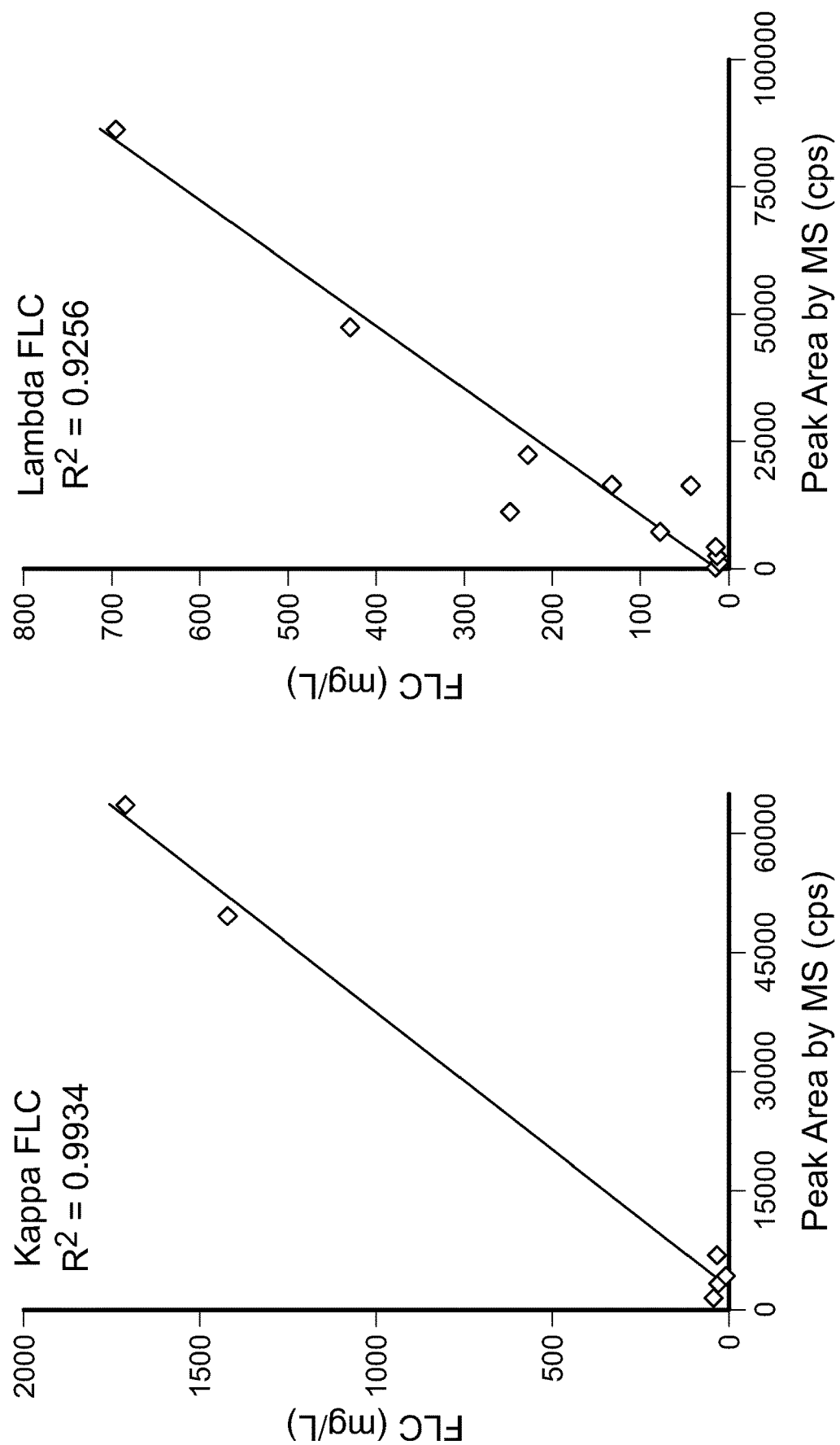
FIG. 16. Shows the Linear regression analysis of AL patient FLC. The graphs were generated by plotting the concentration of the FLC by nephelometry against the peak area for the FLC observed in the mass spectrometer. The $R^2$ correlation coefficients are listed for kappa and lambda FLC with outliers removed.

Table 2 displays each patient's FLC listed by isotype (kappa first followed by lambda) along with the kappa/lambda ratio, isotype specific FLC concentration (mg/L), and the corresponding peak area (counts per seconds) of each monoclonal FLC observed in the mass spectrometer. The peak areas listed in the table were found using the same method used to determine linearity and precision for the purified FLC spiked into normal serum. The table shows that the isotype specific FLC concentrations are much higher in the Pavia patient cohort as compared to the Mayo cohort and that the FLC concentrations are present over several orders of magnitude. A linear regression analysis was performed to determine the correlation between the peak areas of each patient's monoclonal FLC found using the methods disclosed herein with the concentration of FLC determined using nephelometry and the results are shown in FIG. 16. The linear regression marked Kappa FLC has 2 outliers removed out of a total of 8; patients Pavia 4 and Mayo 10. The linear regression marked Lambda FLC has 4 patient outliers removed out of a total of 15; patients Pavia 7, Pavia 13, Pavia 14, and Pavia 15.

TABLE 2

| Biobank | Isotype | k/λ ratio | FLC mg/mL | MS Peak Areas (cps) |
|---------|---------|-----------|-----------|---------------------|
| Pavia 3 | K | 845 | 1420 | 49650 |
| Pavia 4 | K | 73.4 | 1350 | 6062 |
| Pavia 11 | K | 118 | 1710 | 63680 |
| Mayo 1 | K | 7.49 | 8 | 4190 |
| Mayo 3 | K | 11.9 | 28 | 3408 |
| Mayo 4 | K | 27.7 | 43 | 1573 |
| Mayo 9 | K | 51.9 | 34 | 6919 |
| Mayo 10 | K | 42.1 | 69 | 38884 |
| Pavia 1 | L | 0.05 | 248 | 11510 |
| Pavia 2 | L | 0.07 | 695 | 86320 |
| Pavia 6 | L | 0.02 | 429 | 47500 |
| Pavia 7 | L | 0.01 | 1140 | 59150 |
| Pavia 10 | L | 0.08 | 228 | 22450 |
| Pavia 12 | L | 0.07 | 132 | 16500 |
| Pavia 13 | L | 0.017 | 477 | 94520 |
| Pavia 14 | L | 0.01 | 98 | 31390 |
| Pavia 15 | L | 0.04 | 733 | 1284 |
| Mayo 2 | L | 0.01 | 15 | 4372 |
| Mayo 5 | L | 0.03 | 43 | 16650 |
| Mayo 7 | L | 0.01 | 77 | 7500 |
| Mayo 8 | L | 0.11 | 11 | 1300 |
| Mayo 11 | L | 0.02 | 14 | 490 |
| Mayo 12 | L | 0.05 | 13 | 2711 |

Discussion

Example 7 demonstrates that microLC-ESI-Q-TOF mass spectrometry can provide accurate molecular mass information on intact FLC and quantitative information for a specific monoclonal FLC. Furthermore, information on post-translation modifications can also be defined using mass spectrometry. This combination of powerful analytical features makes mass spectrometry a comprehensive platform for monitoring monoclonal FLC. Further, example 7 demonstrates that the methods disclosed herein can readily identify a monoclonal FLC from the polyclonal background and identify the isotype of the light chain by top-down MS eliminating the need for reference ranges to determine if a monoclonal FLC is present. Further, example 7 demonstrates that the methods disclosed herein can be used to monitor dimer/monomer ratios as well as PTM's.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying one or more immunoglobulin free light chains in a sample, the method comprising:
   a. providing a sample, wherein the sample is a serum sample, a cerebrospinal fluid sample, or a whole blood sample;
   b. enriching free light chains from the sample to obtain an enriched sample;
   c. subjecting the enriched sample to a top-down mass spectrometry technique to obtain a mass spectrum of the sample;
   d. identifying the presence of the one or more immunoglobulin free light chains; and
   e. measuring the concentration of the one or more immunoglobulin free light chains in the sample.

2. The method of claim 1, wherein the sample is suspected to comprise an immunoglobulin free light chain.

3. The method of claim 1, wherein the one or more immunoglobulin free light chains are selected from the group consisting of free kappa light chains, free lambda light chains, and mixtures thereof.

4. The method of claim 1, wherein the immunoglobulin free light chain is a free kappa light chain.

5. The method of claim 1, wherein the method comprises identifying at least two types of free kappa light chains.

6. The method of claim 1, wherein the immunoglobulin free light chain is a free lambda light chain.

7. The method of claim 1, wherein the method comprises identifying at least two types of free lambda light chains.

8. The method of claim 1, wherein the one or more immunoglobulin free light chains comprises at least one of a glycosylated immunoglobulin free light chain, a cysteinylated immunoglobulin free light chain, and a glutathionylated immunoglobulin free light chain.

9. The method of claim 1, wherein the identifying the one or more immunoglobulin free light chains occurs in the presence of a polyclonal background.

10. The method of claim 1, wherein the method further comprises identifying at least one immunoglobulin free light chain dimer.

11. The method of claim 1, further comprising contacting the sample with a reducing agent prior to subjecting the sample to the mass spectrometry technique.

12. The method of claim 11, wherein the reducing agent is selected from the group consisting of dithiothreitol (DTT), reduced glutathione, β-mercaptoethanol, tris(2-carboxyethyl) phosphine hydrochloride, cysteine, 2-mercaptoethylamine, 3-mercaptopropionic acid, and mixtures thereof.

13. The method of claim 11, wherein the reducing agent is dithiothreitol.

14. The method of claim 1, wherein the method does not include contacting the sample with a reducing agent.

15. The method of claim 1, wherein the mass spectrometry technique is LC-MS/MS.

16. The method of claim 15, wherein the LC-MS/MS technique comprises a quadrupole time-of-flight mass spectrometer.

17. The method of claim 1, wherein the sample is a serum sample.

18. The method of claim 1, wherein the sample is from a single subject and the method further comprises diagnosing a disorder in the subject wherein the disorder is a plasma cell dyscrasia.

19. The method of claim 1, wherein the sample is from a single subject and the method further comprises diagnosing a disorder in the subject wherein the disorder is at least one of a multiple myeloma or a light chain amyloidosis.

20. The method of claim 1, wherein the sample is from a single subject and the method further comprises diagnosing a disorder in the subject wherein the disorder is at least one of multiple myeloma, monoclonal gammopathy of undetermined significance, B-cell chronic lymphocytic leukemia, Waldenstroms macrogloblinemia, amyloid light chain amyloidosis, or non-secretory myeloma.

21. The method of claim 1, wherein the sample is from a single subject and the method further comprises distinguishing an auto-immune response from a monoclonal gammopathy in the subject.

22. A method for identifying one or more immunoglobulin free light chains in a sample, the method comprising:

a. providing a sample, wherein the sample is a serum sample, a cerebrospinal fluid sample, or a whole blood sample;

b. enriching free light chains from the sample to obtain an enriched sample;

c. contacting the enriched sample with a reducing agent;

d. subjecting the sample to a top-down mass spectrometry technique to obtain a mass spectrum of the sample;

e. identifying the presence of one or more immunoglobulin free light chains; and f. measuring the concentration of the one or more immunoglobulin free light chains in the sample.

* * * * *